United States Patent [19]
Yasukawa et al.

[11] Patent Number: 5,735,800
[45] Date of Patent: Apr. 7, 1998

[54] WRIST-WORN PORTABLE DEVICE AND A WRIST-WORN PULSE WAVE MEASURING DEVICE

[75] Inventors: Naoaki Yasukawa, Suwa; Masayuki Kawata, Chiba, both of Japan

[73] Assignees: Seiko Epson Corporation, Tokyo; Seiko Instruments Inc., Chiba-ken, both of Japan

[21] Appl. No.: 646,456

[22] Filed: May 8, 1996

[30] Foreign Application Priority Data

May 12, 1995 [JP] Japan ................. 7-114962
May 12, 1995 [JP] Japan ................. 7-114963

[51] Int. Cl.$^6$ ........................................ A61B 5/02
[52] U.S. Cl. .................. 600/503; 600/310; 600/476; 600/479; 600/502
[58] Field of Search ............. 128/690, 664–667, 128/633; 224/165, 172

[56] References Cited

U.S. PATENT DOCUMENTS 3,326,429  6/1967  Camoletti ..................... 224/171
4,185,621  1/1980  Morrow ....................... 128/690
4,425,921  1/1984  Fujisaki ....................... 128/690

*Primary Examiner*—Jennifer Bahr
*Assistant Examiner*—David M. Ruddy
*Attorney, Agent, or Firm*—Eric B. Janofsky

[57] ABSTRACT

For the purpose of providing, by only improving the shape of the device body, at a low cost and without impairing user comfort a wrist-worn portable device and a wrist-worn pulse wave measuring device whereby the device body does not turn unnecessarily around the wrist. A wrist-worn pulse wave measuring device 1 attaches device body 10 by means of wrist band 12 to the wrist, and attaches sensor unit 30 to the base of a finger by means of a band for holding the sensor. At the end of cable 20 leading from sensor unit 30 is formed connector piece 80, which is attached by simply sliding connector 70 in the direction of twelve o'clock. Because device body 10 has a turning stop 108 forming an approximately 115° angle to the back, device body 10 will not turn unnecessarily even if it is turned in the direction of six o'clock or twelve o'clock on a wristwatch.

11 Claims, 16 Drawing Sheets

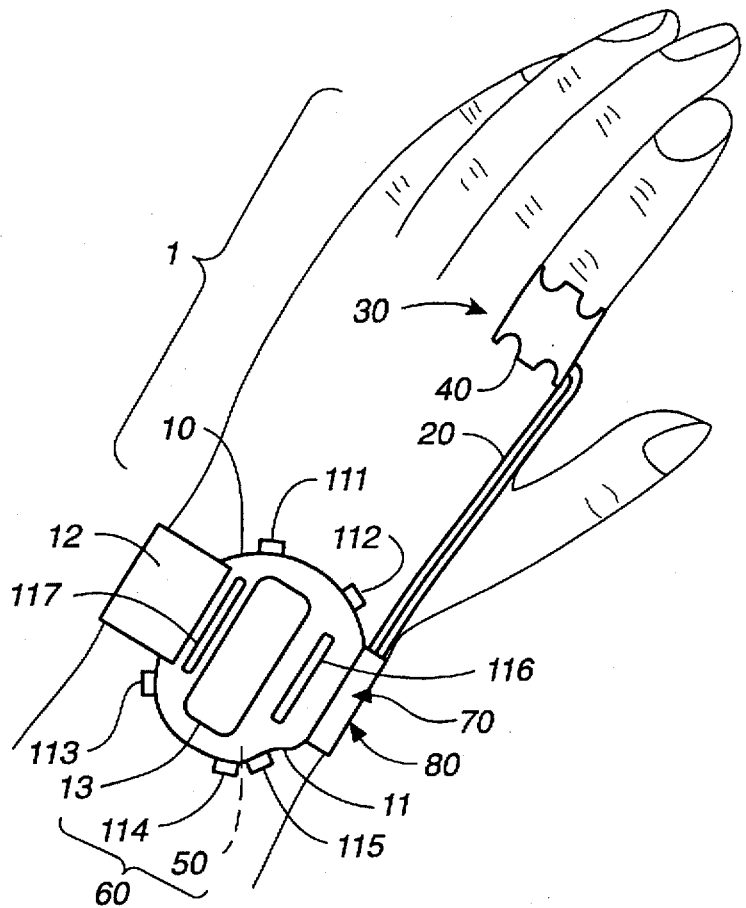
FIG._1A
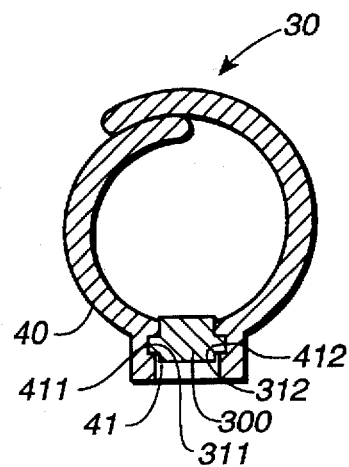
FIG._1B

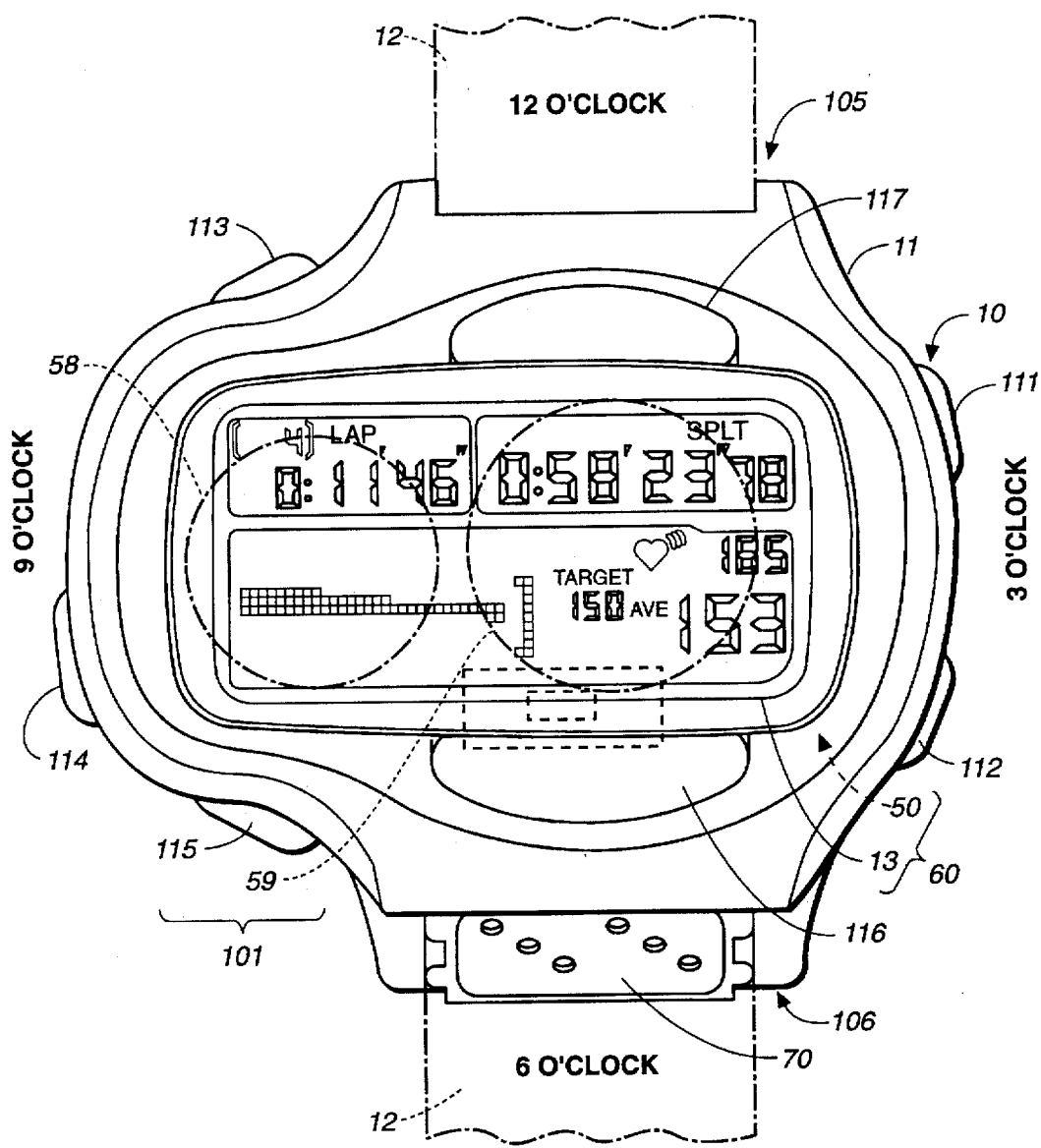
FIG._2

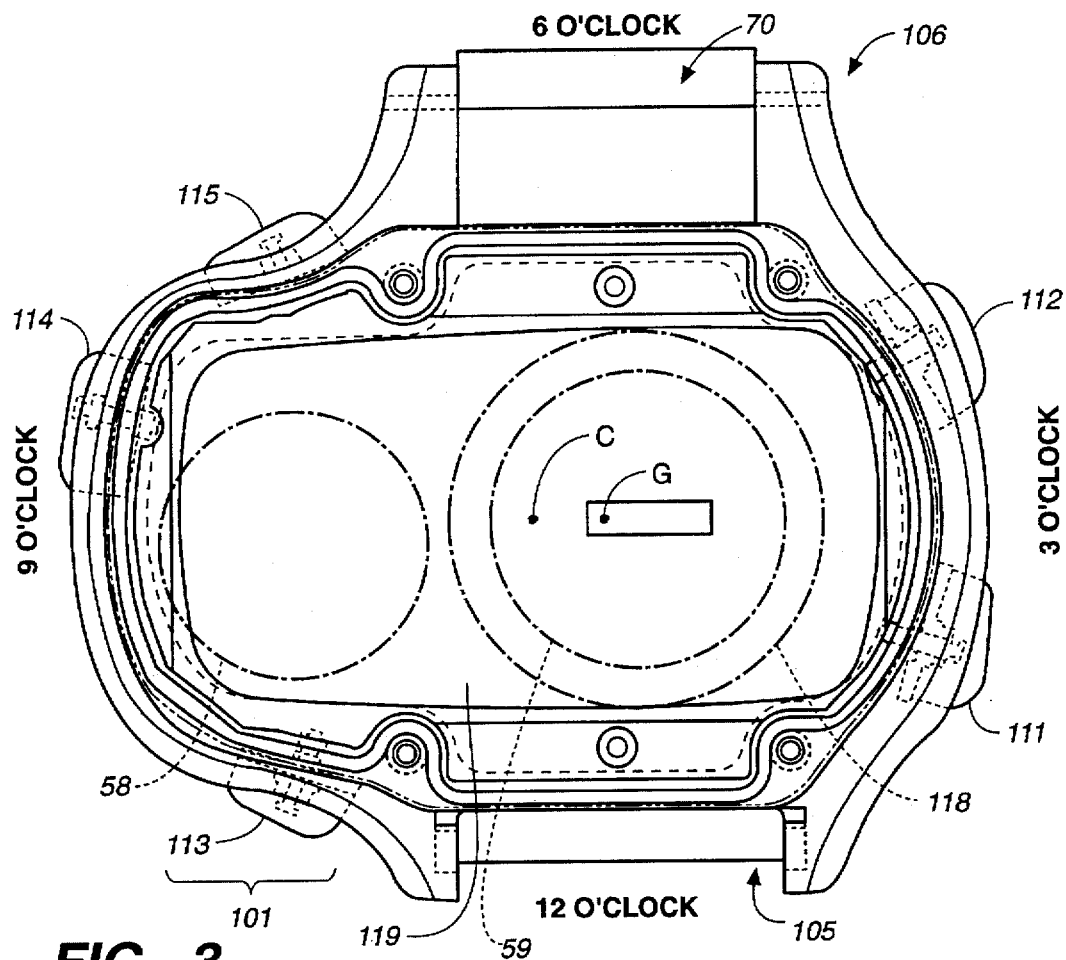
FIG._3
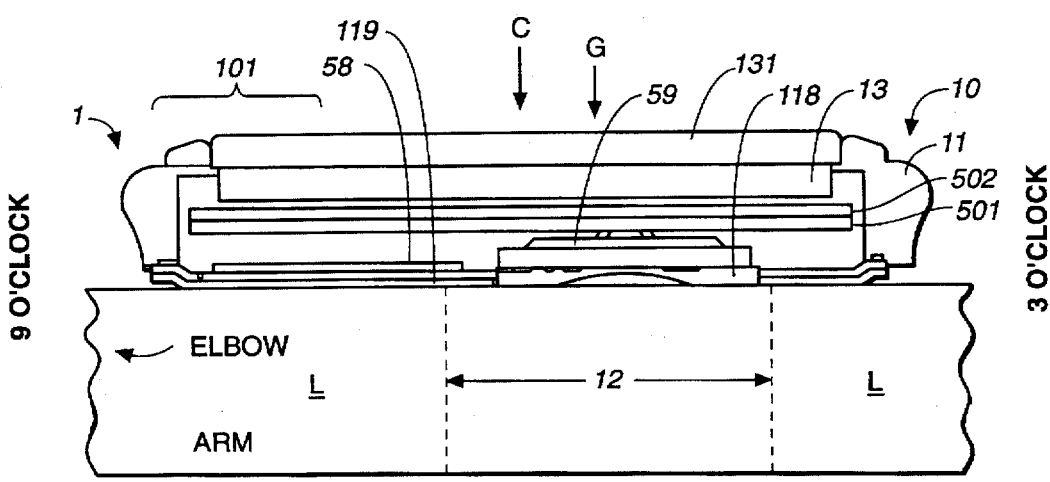
FIG._4

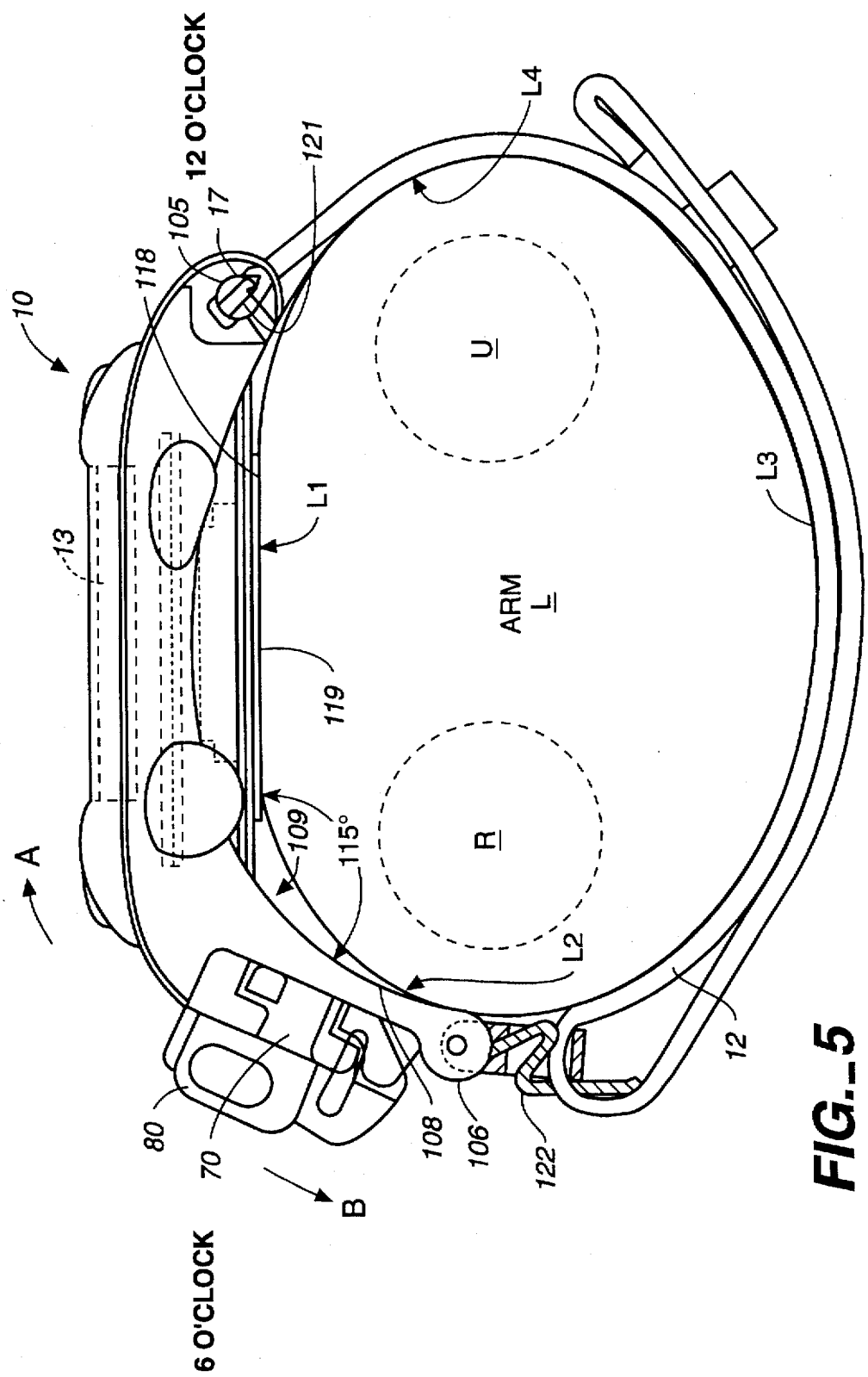
FIG._5

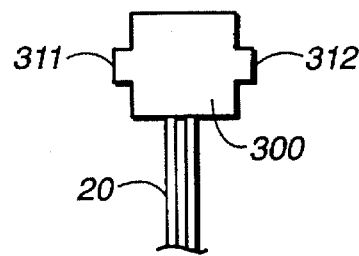
FIG._6A
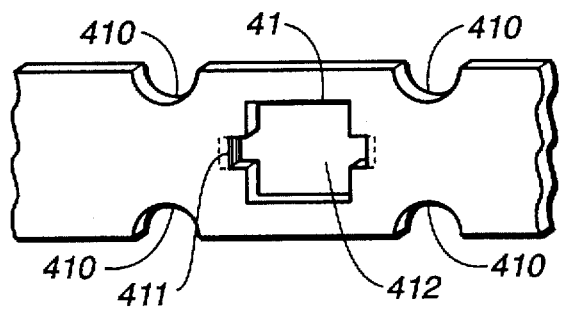
FIG._6B
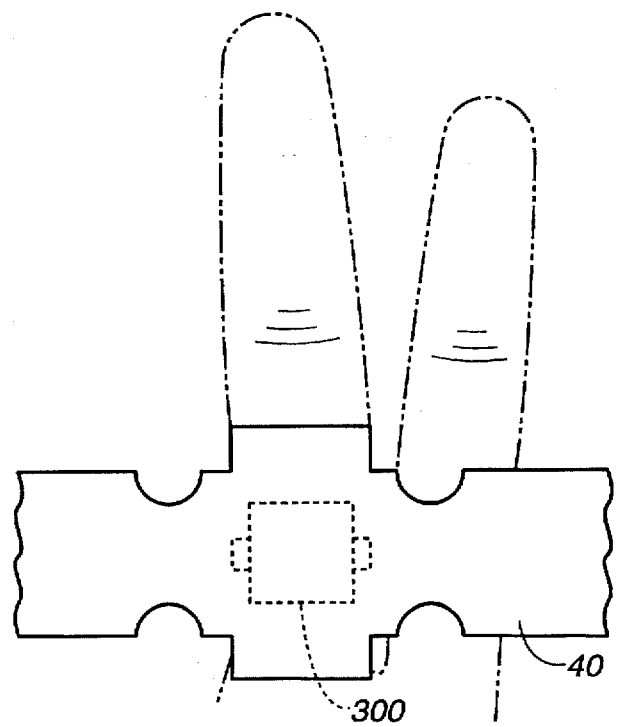
FIG._6C

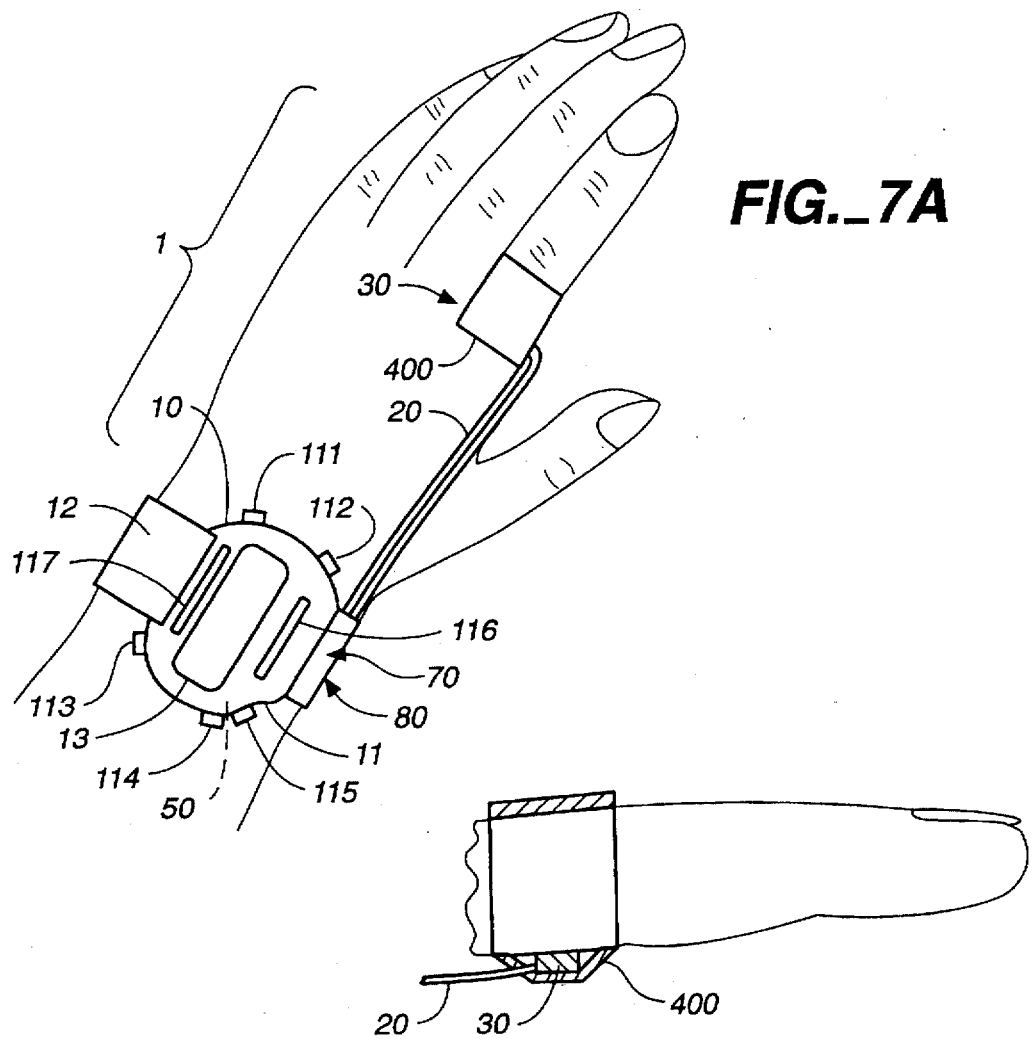
FIG._7A
FIG._7B
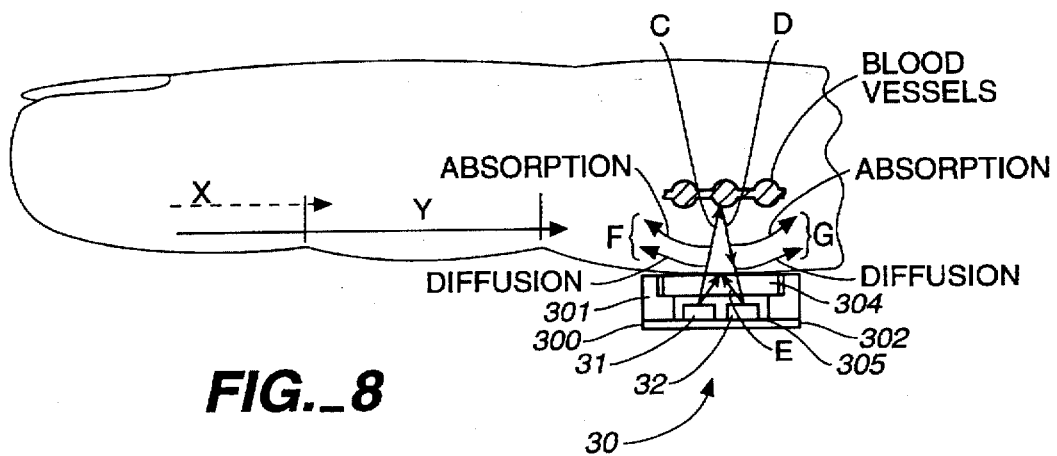
FIG._8

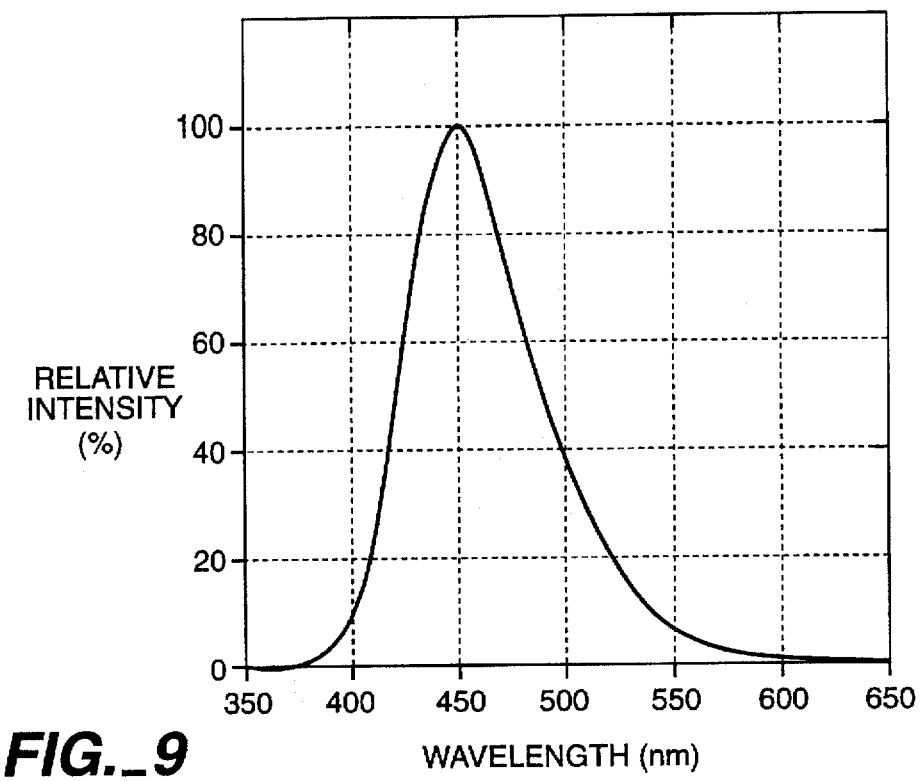
FIG._9
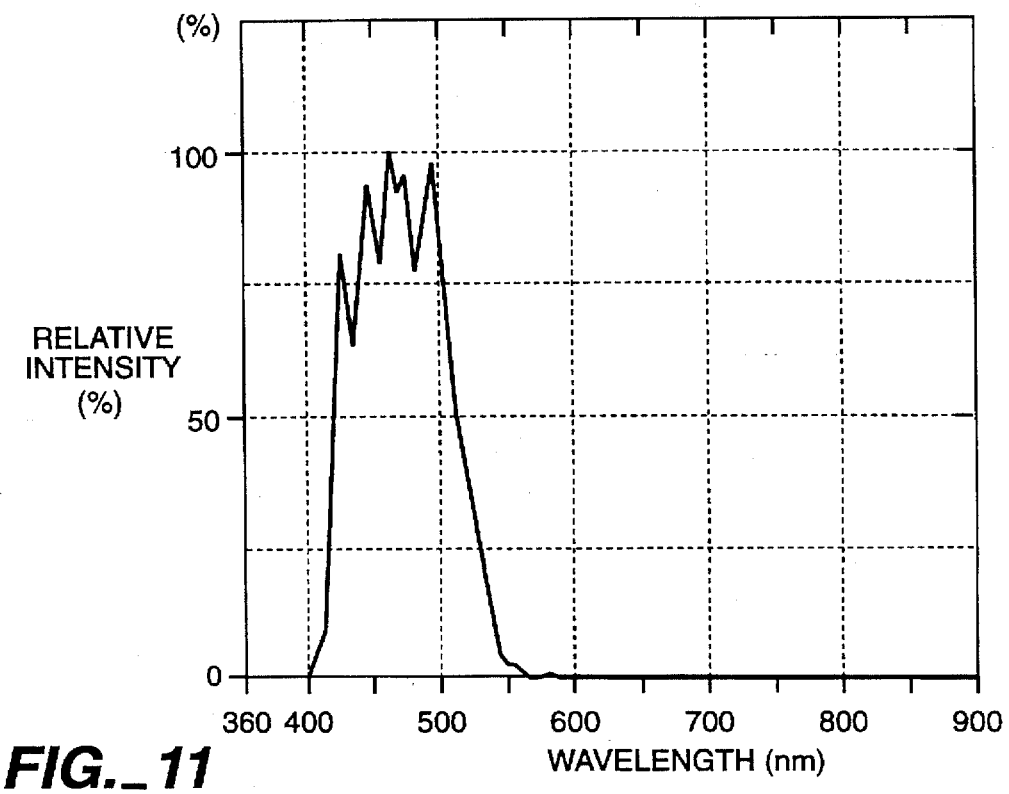
FIG._11

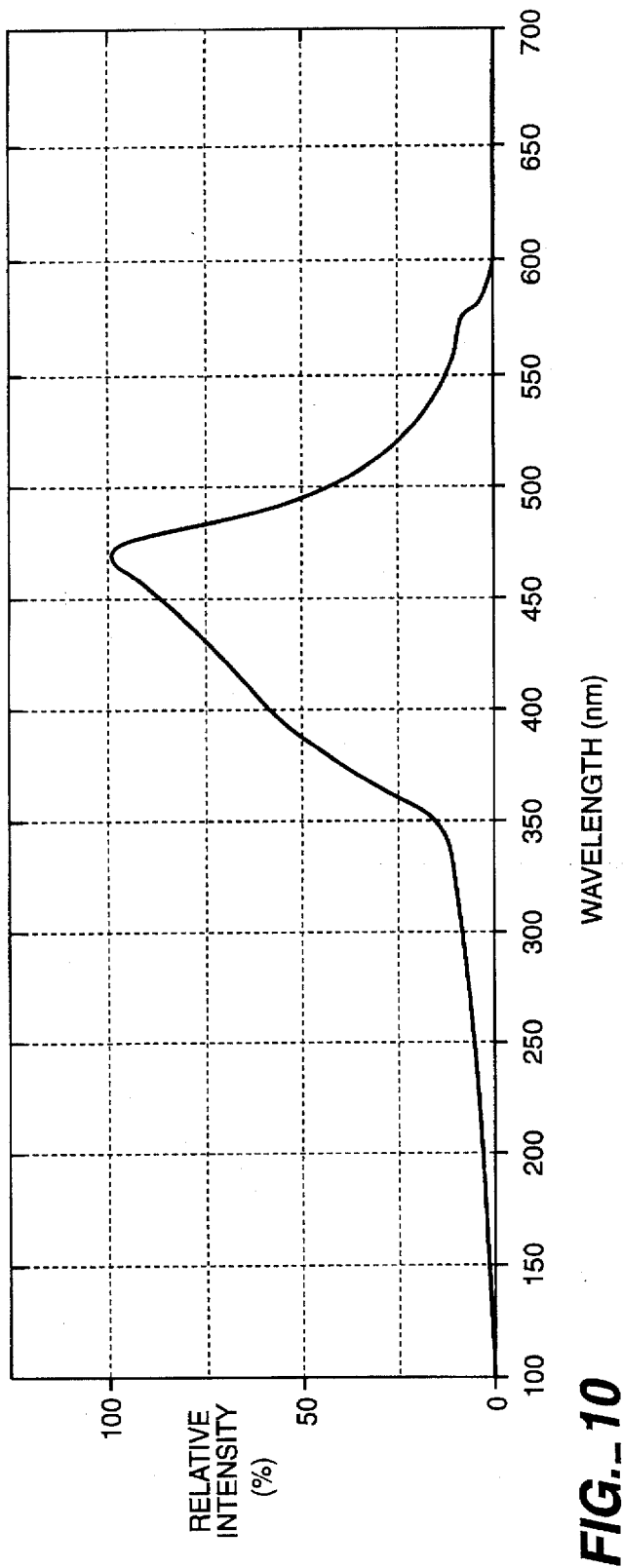
FIG._10
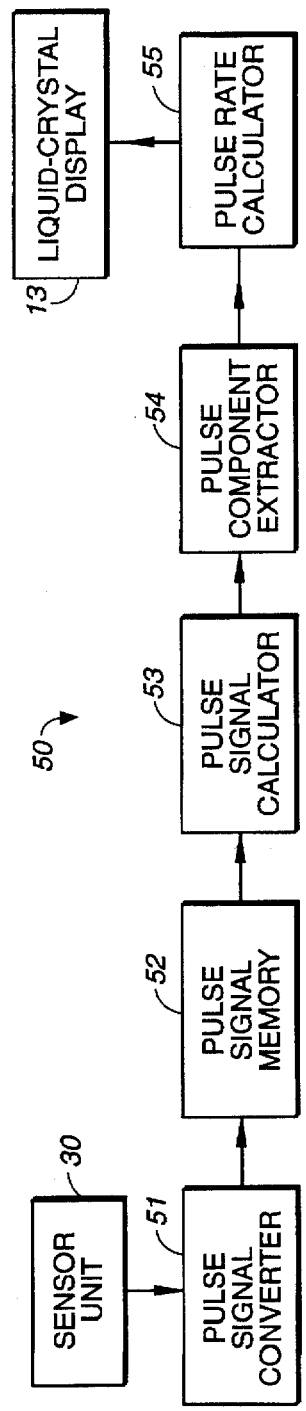
FIG._12

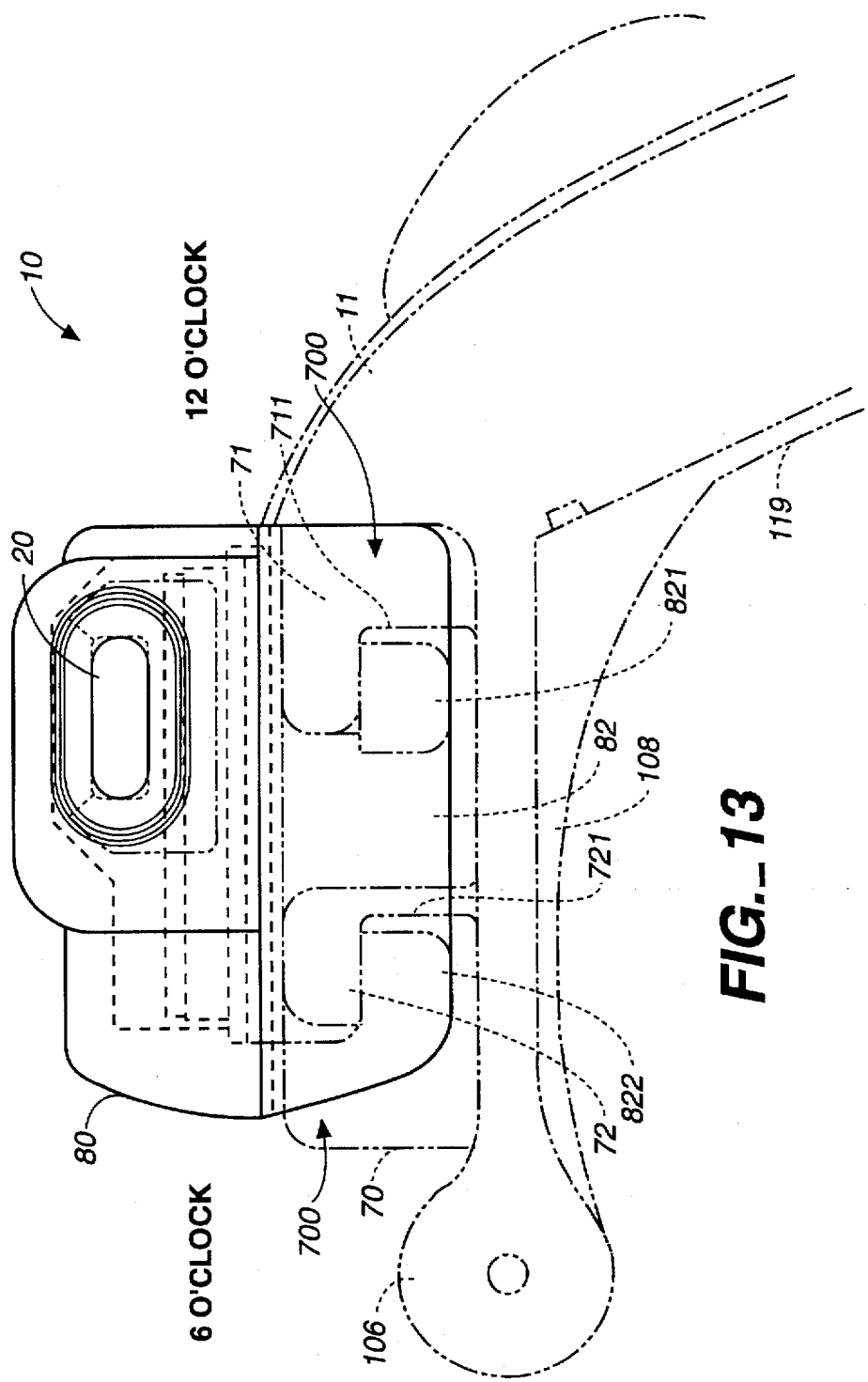
FIG._13

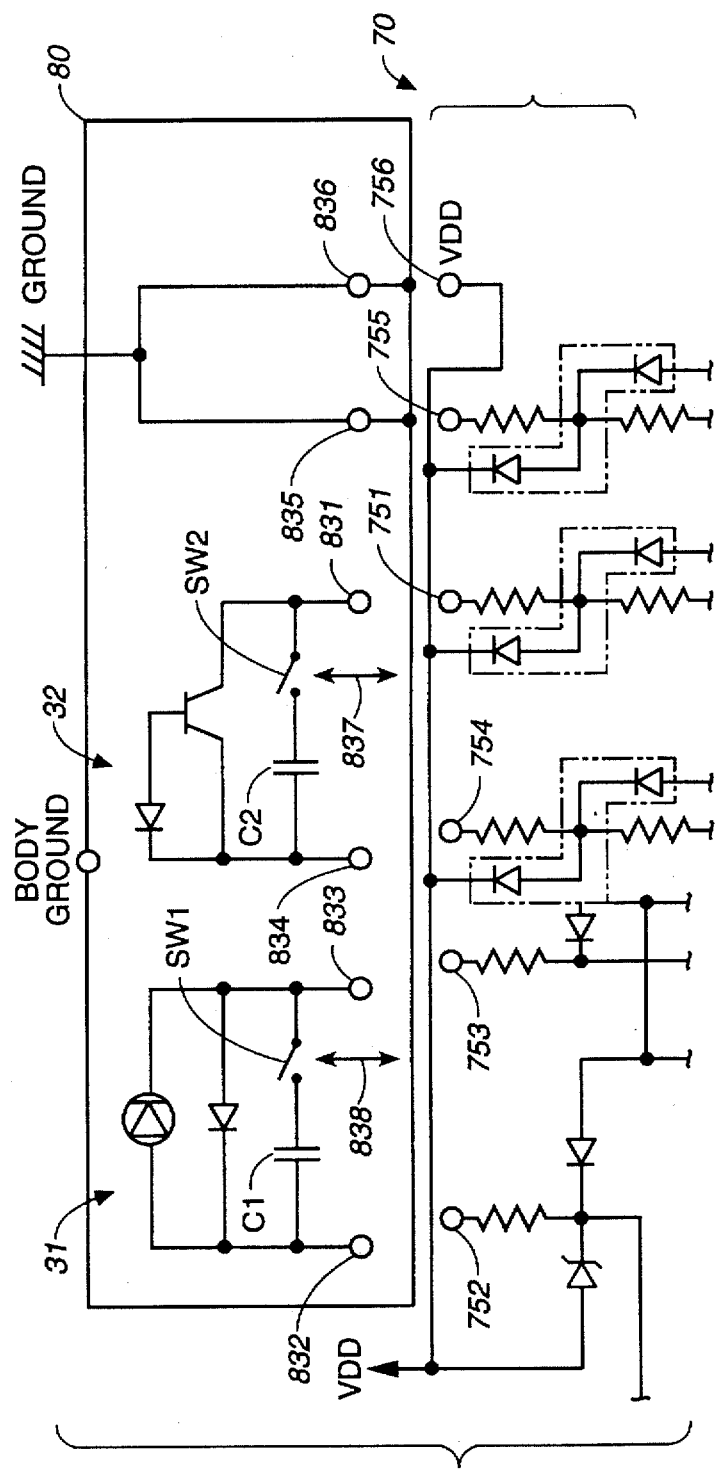
FIG._14

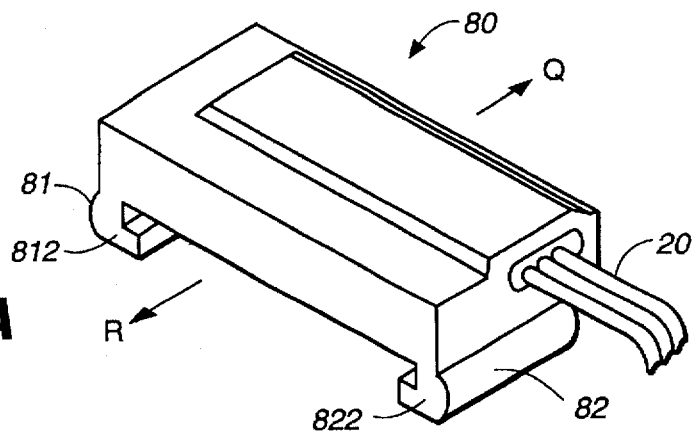
FIG._15A
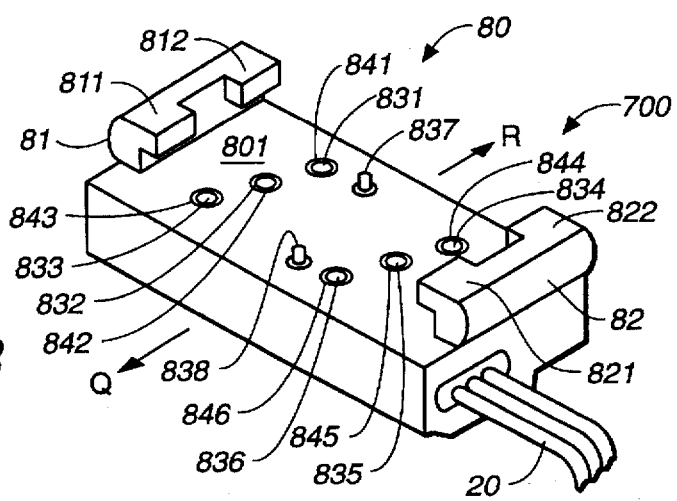
FIG._15B
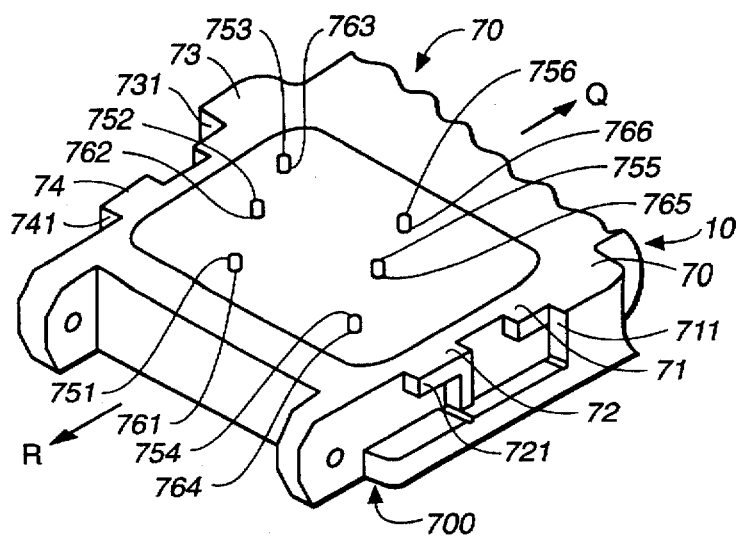
FIG._16

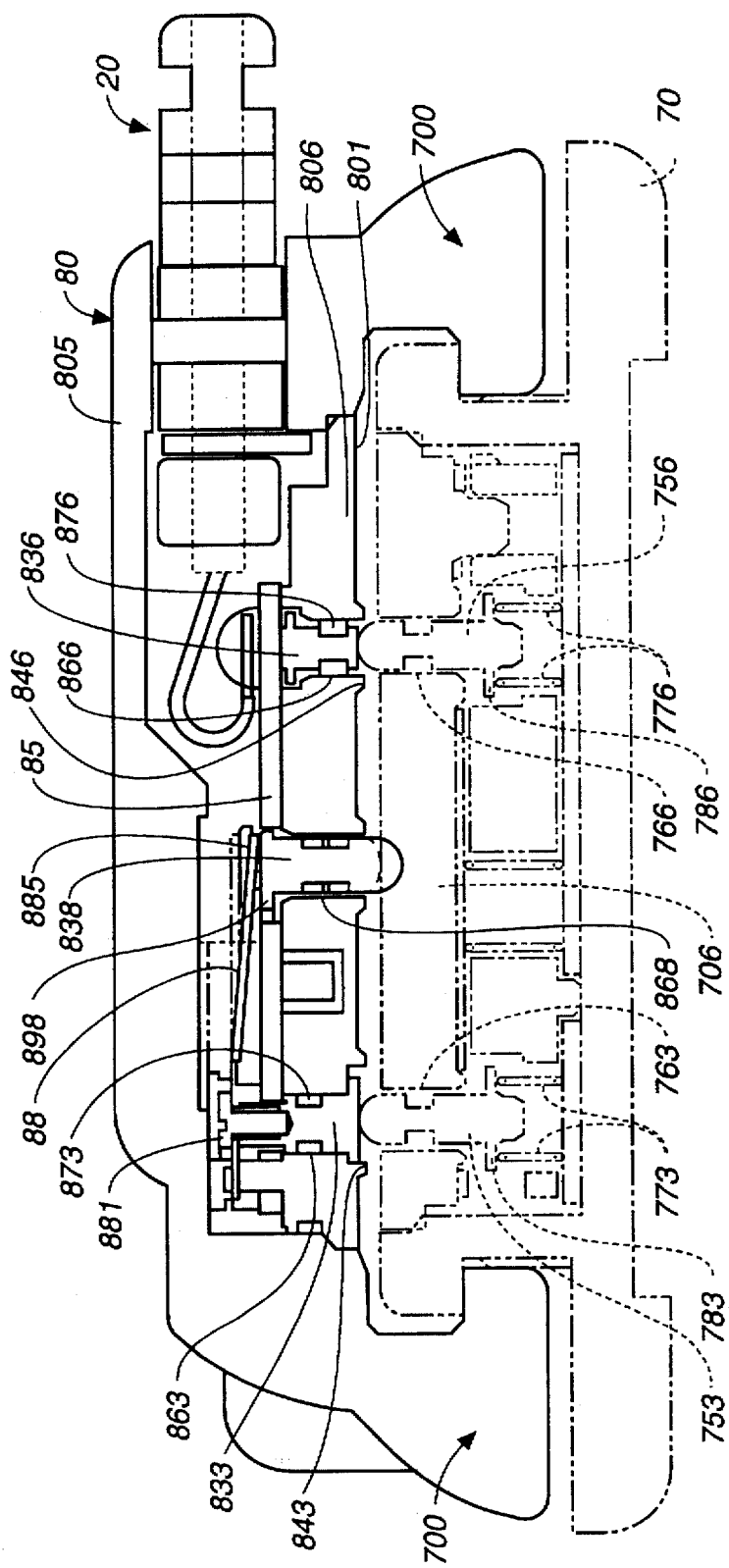
FIG._17

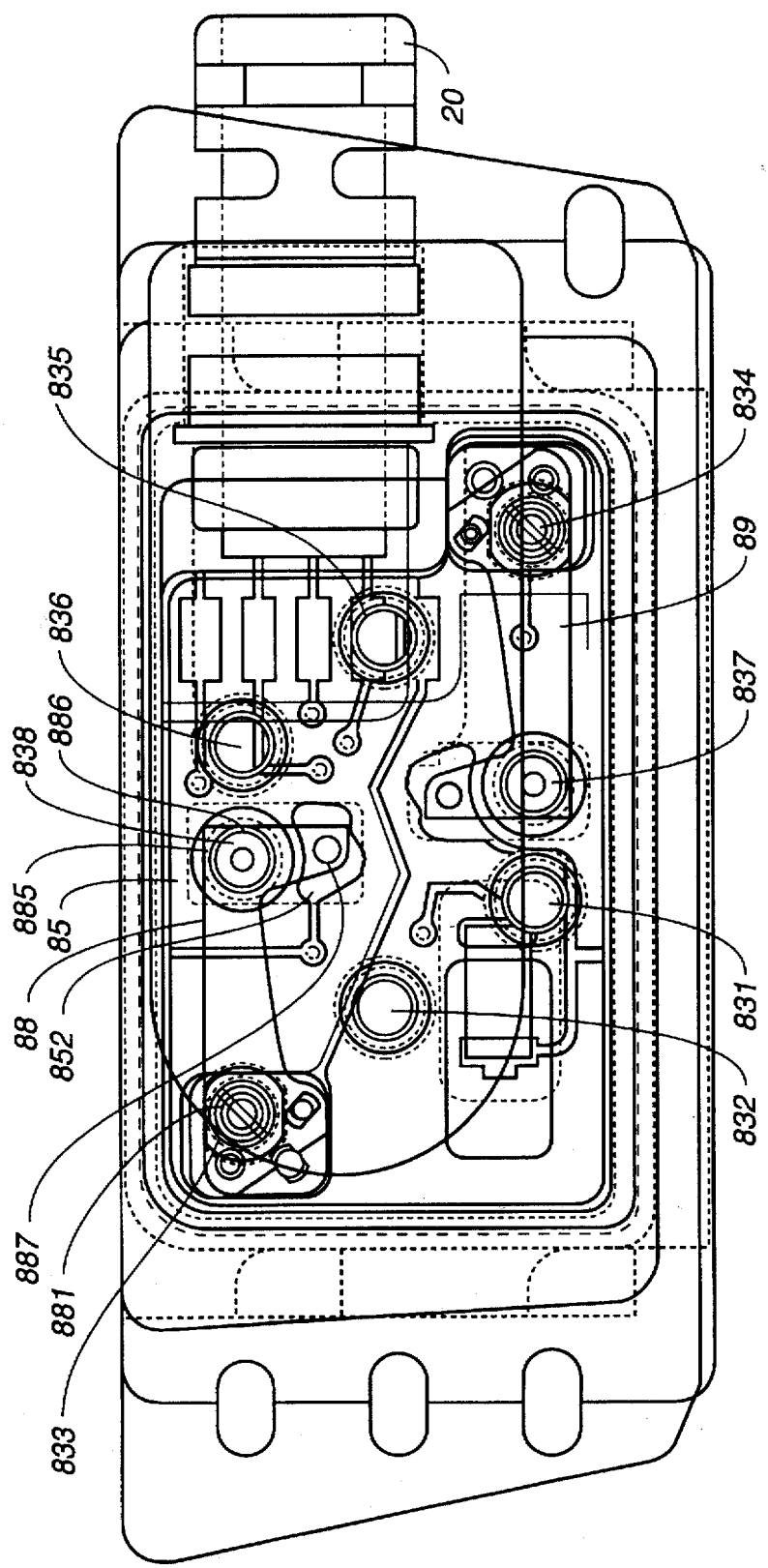
FIG._18

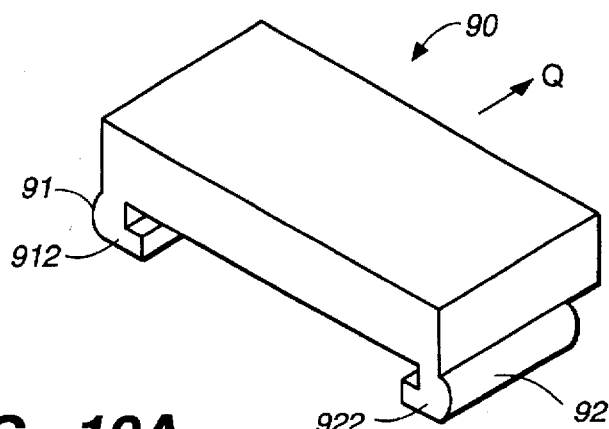
FIG._19A
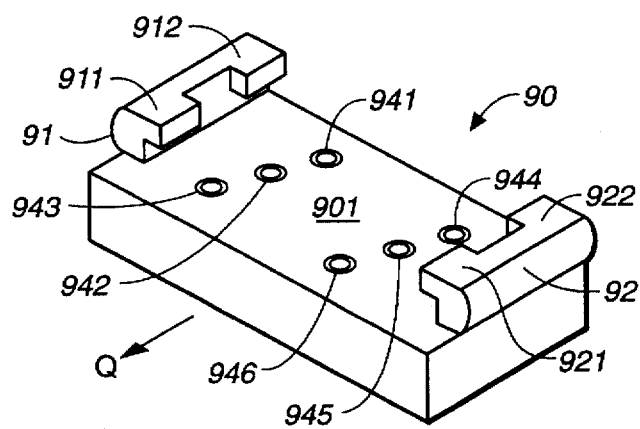
FIG._19B
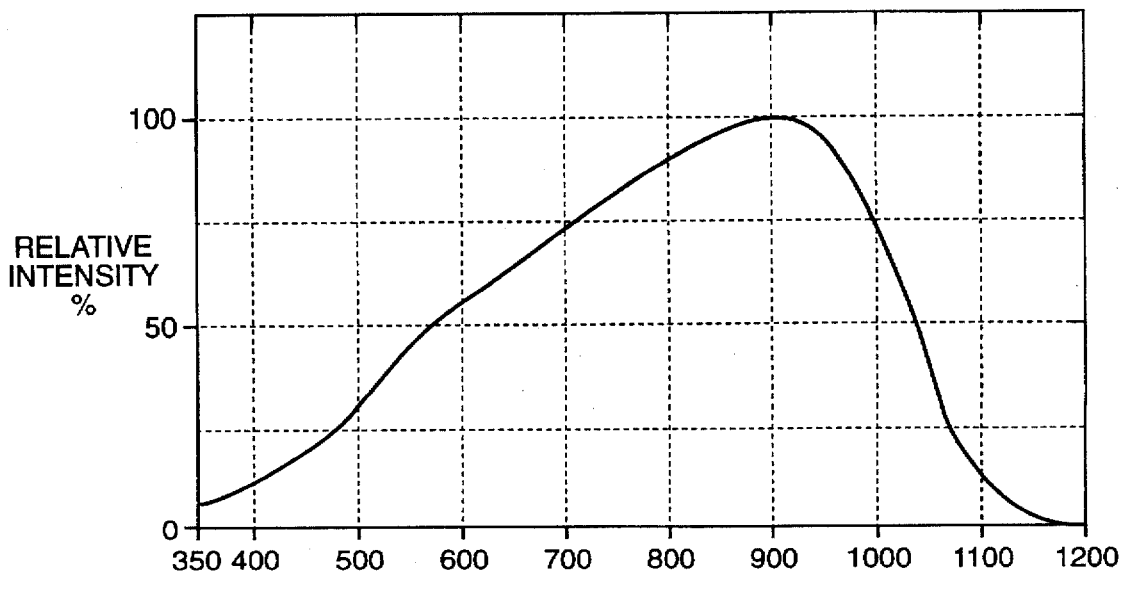
FIG._21

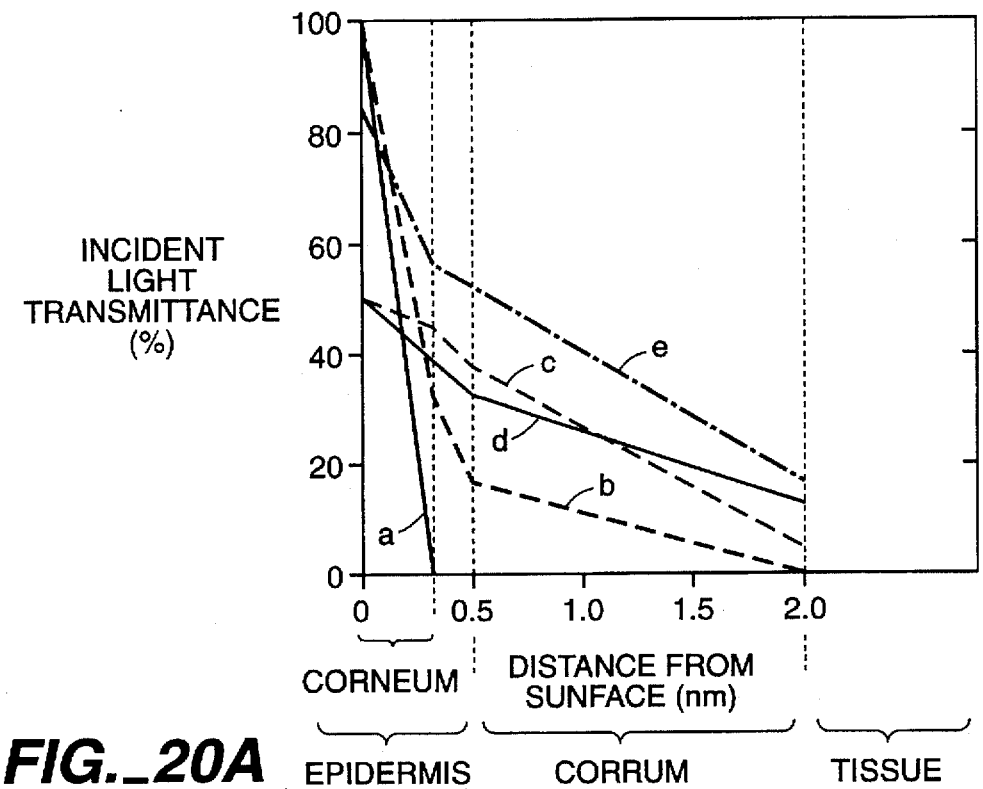
FIG._20A
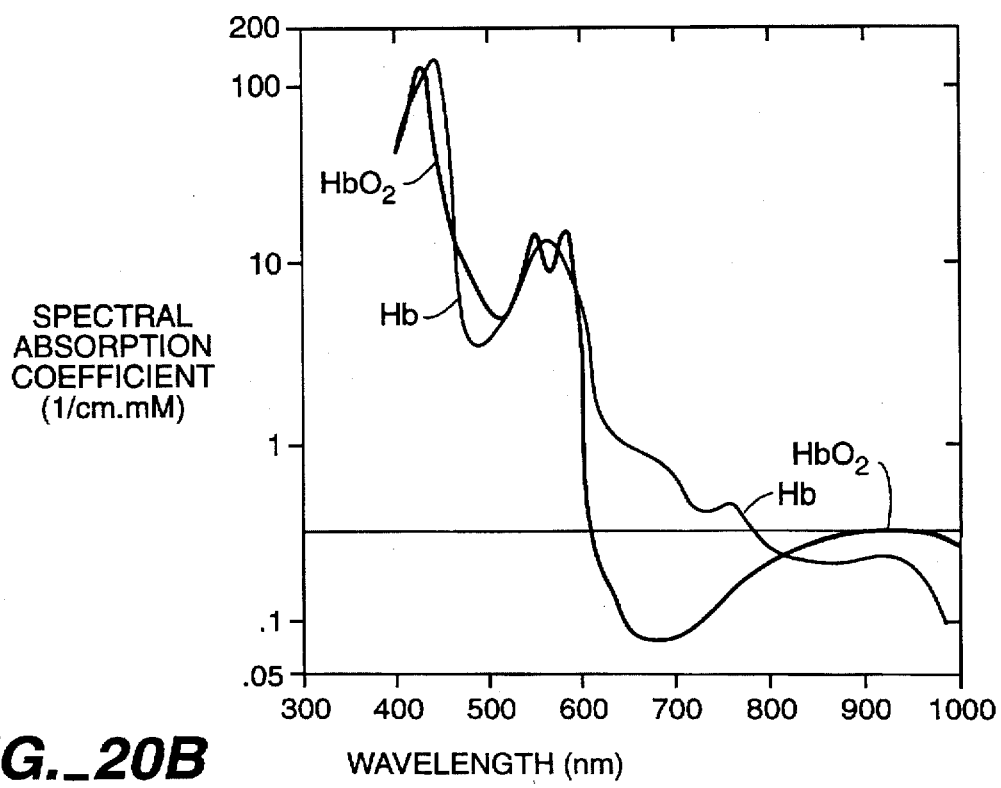
FIG._20B

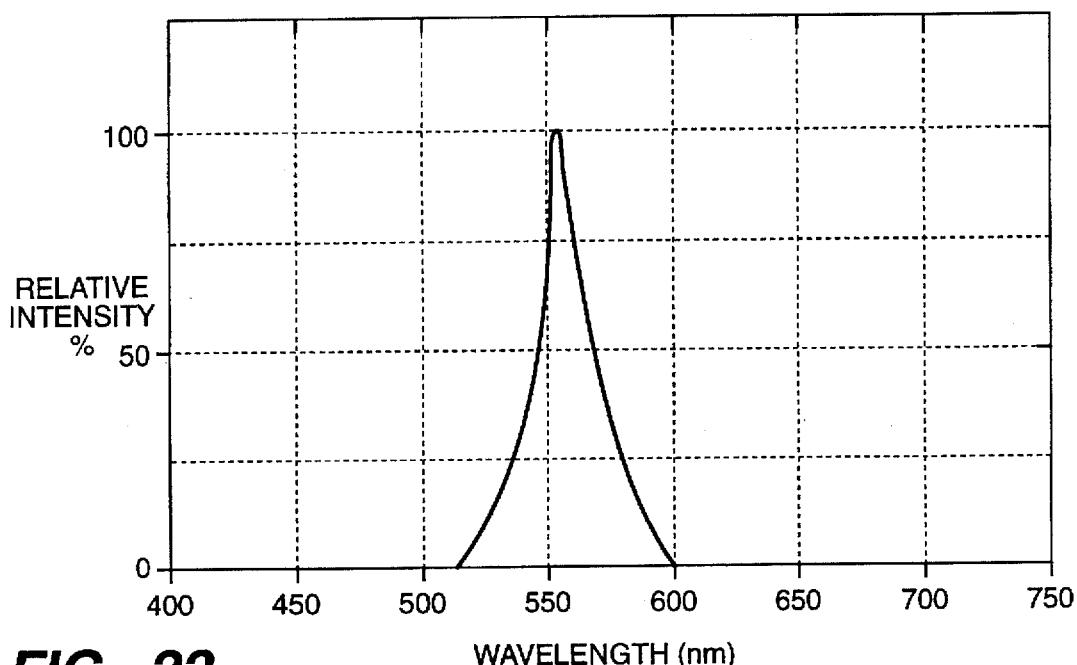
FIG._22
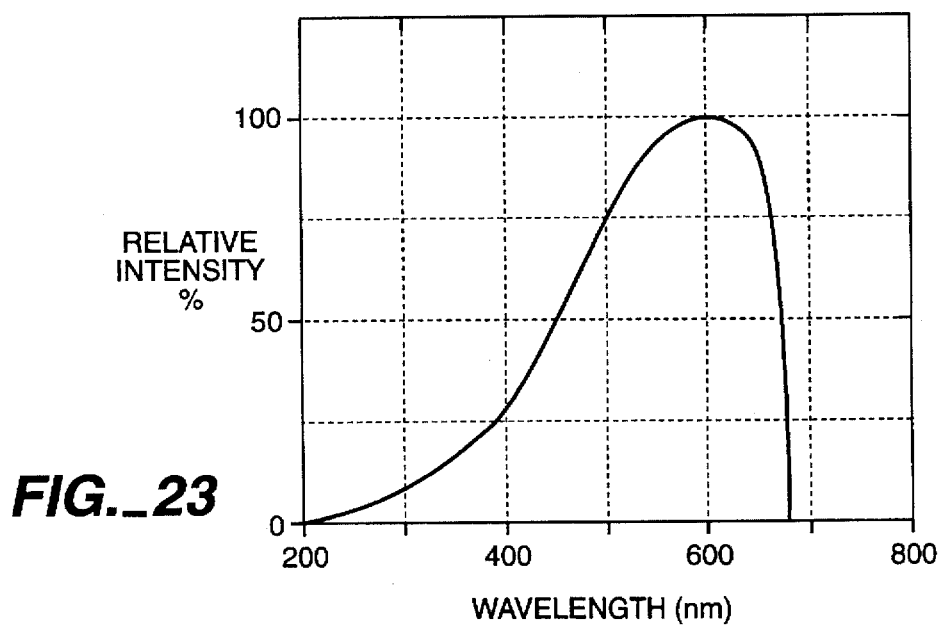
FIG._23
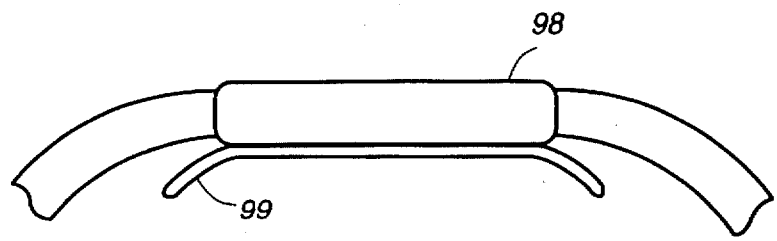
FIG._24

WRIST-WORN PORTABLE DEVICE AND A WRIST-WORN PULSE WAVE MEASURING DEVICE

BACKGROUND OF THE INVENTION

1. Field of the Invention

The present invention relates generally to a wrist-worn portable device capable of displaying, for example, the time. More particularly, the present invention relates to a wrist-worn pulse wave measuring device capable of displaying the pulse rate and other pulse information. More specifically, the present invention relates to the structure of the device body thereof.

2. Description of the Related Art

Wrist-worn portable devices capable of displaying various information include wrist watches, runner's wrist watches equipped with a stopwatch function, portable wrist radios equipped with a clock function, and devices for optically detecting changes in the blood level for displaying pulse information, such as the pulse rate, based on the detection results. With optical pulse wave measuring devices such as this, a sensor unit comprising a light-emitting element, such as an LED (light-emitting diode), and an optical receptor, such as a phototransistor, is fastened to a finger, etc., the change in blood volume is detected as the change in the blood quantity by means of the phototransistor detecting the light emitted from the LED and reflected from the finger (blood vessels), and the pulse count is displayed based on the detection result. Each of these wrist-worn portable devices is alike, however, in that, like a wristwatch, the device body having a flat back surface is held on the wrist by a wrist band. The wrist band is connected at positions in the six o'clock and twelve o'clock positions of the device body centered to the three o'clock and nine o'clock positions.

However, no consideration for preventing the device body from rotating around the wrist has been given in the shape of the device body in these conventional wrist-worn portable devices, and the device body tends to rotate unnecessarily around the arm as the device is worn on the wrist. For example, when a user goes running wearing a portable wrist device on the wrist, the device body can slip easily of its own weight toward the outside of the arm. As a result, despite the number of functions that can be used portably, conventional wrist-worn portable devices have the problem of being difficult to use because the display surface shifts, making viewing difficult. In particular, it may not be possible to read the display if the device body shifts when using a liquid crystal display because of the narrow viewing angle. It may also not be possible to see the display if the elbow is not bent unnaturally.

Furthermore, because wristwatches for exercisers, such as runners, are naturally worn while jogging or running a marathon, and wrist-worn pulse wave measuring devices also tend to be used to measure the pulse while running, usability is extremely poor when the device body is able to turn unnecessarily around the wrist while running.

Referring to FIG. 24, a structure comprising thin wall plate 99 is provided for preventing device body 98 from turning around the wrist. Thin plate 99 is curved in shape to match the shape of the wrist on the back of device body 98. Plate 99 is flexible and deforms against the wrist when wearing device body 98 on the wrist With this structure, however, a separate plate 99 is fastened to device body 98, thus requiring more time during the assembly process. Because plate 99 fits tightly to the skin completely around the wrist, it may become hot and cause sweating, creating a problem with poor user comfort. In addition, this structure does not prevent rotation around the wrist when the wrist is thin, and when the wrists are thick, the fit is tight and comfort is poor.

As large scale integration improves, wrist-worn devices will have added functionality. Therefore it is also necessary to add a graphic display area or otherwise increase the display size in order to communicate information easily with wrist-worn portable devices. If functions are to be increased, it is also necessary to increase the size of the device body, but the device body gets in the way when the thickness thereof is increased. The device body is therefore enlarged in the planar direction, but if the device is to be worn on the wrist, it is difficult to greatly increase the size in the six o'clock and twelve o'clock directions. By necessity the device is therefore enlarged in the three o'clock and nine o'clock directions; because enlargement in this direction follows the arm, it is less of a problem. As a result, a horizontally long case in which the length in the three o'clock and nine o'clock directions is greater than the length in the six o'clock and twelve o'clock directions is used.

However, if the device body is simply enlarged in the horizontal direction, the structure will protrude greatly in the three o'clock direction. Thus, each time the wrist is bent with the wrist-worn portable device worn on the wrist, the back of the hand contacts the device case, creating discomfort, possibly injuring the back of the hand if the user falls down, and thus resulting in a structure that is not suited to wearing on the wrist.

OBJECTS OF THE INVENTION

Therefore, it is an object of the present invention to overcome the aforementioned problems.

It is another object of the present invention to provide, by only improving the shape of the device body, at a low cost and without impairing user comfort a wrist-worn portable device and a wrist-worn pulse wave measuring device whereby the device body does not turn unnecessarily around the wrist.

It is a further object of the invention to provide a wrist-worn portable device and a wrist-worn pulse wave measuring device suited to wearing on the wrist even when using a horizontally long device case.

SUMMARY OF THE INVENTION

According to an aspect of the present invention, to achieve by only improving the shape of the device body a low-cost wrist-worn portable device and a wrist-worn pulse wave measuring device, whereby the device body does not turn unnecessarily around the arm, the wrist-worn portable device comprising a device body having a display unit for displaying information and a wrist band for attaching this device body to the arm is provided in the device body a main case having a back member able to fit tight to the top of the wrist (i.e., that part of the wrist circumference on the some side as the back of the hand), and a turning stop extending from the main case in the direction of six o'clock on a wristwatch, and controlling rotation of the device body around the wrist by contacting the side of the wrist.

It is sufficient here if the back member of the main case can fit tightly against the top of the wrist, and during use the wrist-worn portable device may be worn with the device body positioned to the bottom of the wrist (i.e., that part of the wrist circumference on the same side as the palm of the hand). Furthermore, "in the direction of something-o'clock" on a wristwatch in the present invention naturally refers to the orientation of the device body, and does not mean that the display on the device body is dial-type analog display.

When the device body of a wrist-worn portable device, such as a wrist-worn pulse wave measuring device, according to the present invention is attached to the arm using the wrist band, the back member of the main case contacts the top of the arm, and the turning stop contacts the side of the arm. Thus, even if the user attempts to turn the device body around the arm in this position, the turning stop remains in contact with the side of the arm and does not shift further, and the back member of the main case remains in contact with the top of the arm and does not shift further. As a result, the device body will not shift when the user goes running wearing the wrist-worn pulse wave measuring device on the arm, and the display can always be read by slightly bending the elbow. User comfort is also not impaired because the device body does not fit tightly completely around the arm. Moreover, because rotation is controlled at two places around the arm, the rotation-stopping effect can be reliably obtained even with thin arms, and there is no discomfort from tightness with thick arms. The turning stop can also be formed integrally with the device body main case. As a result, it is possible by means of the present invention to provide by only improving the shape of the device body a low-cost wrist-worn portable device and a wrist-worn pulse wave measuring device whereby the device body does not turn unnecessarily around the arm and user comfort is not impaired.

In the present invention, the turning stop preferably extends from the main case at an angle within the range from approximately 105° to approximately 125° to the back member of this case.

A wrist-worn portable device of this type can be constructed as a wrist-worn pulse wave measuring device capable of displaying such pulse information as the pulse count on the display by providing a sensor unit of which the light emitting unit and light receptor face the body surface, a cable extending from this sensor unit for inputting the receptor results of the light receptor to the device body, and a data processing circuit built in to the device body for obtaining the pulse information to be displayed on the display based on the receptor results of the light receptor.

The present invention preferably further comprises a connecting means enabling the cable to be freely connected to the device body. With this configuration it is possible to measure the pulse while running by attaching the sensor unit to a finger or other body part, and during everyday living to use the wrist-worn pulse wave measuring device as a conventional wristwatch by simply disconnecting the cable from the connecting means.

In this case it is preferable to provide in the connecting means a connector comprising a first terminal group on the surface of the device body at the part thereof corresponding to the turning stop; a connector member formed at the end of the cable and comprising a second terminal group electrically connecting with each of the terminals in the first terminal group when mounted to the connector as though covering the connector; and an engaging mechanism for holding the connector member to the connector by partially engaging the connector member and connector. Because the part extended to provide the turning stop can be used as is as the connector when thus constructed, it is not necessary to provide unnecessary extended parts on the device body. Moreover, because the connector is positioned at the six o'clock position of a wristwatch, the connecting means is on the front as seen by the user, and operation is simple, when the device body is worn on the arm. Furthermore, because the connecting means does not project from the device body in the three o'clock direction of a wristwatch, the user can freely move the wrist while running, and the hand will not hit the connecting means if the runner falls while running. This is, therefore, safe for the user, and the connecting means will not break. Moreover, because the connector and connector member are coupled by the engaging mechanism, the cable will not accidentally become disconnected while running.

The engaging mechanism also preferably partially engages the connector member and connector when the connector member is slid over the connector in the direction from six o'clock to twelve o'clock on cause wristwatch. Thus constructed, the turning stop simply applies force in the direction making it more difficult to turn the device body even when such a connecting action is performed. The connecting operation can therefore be easily accomplished when attaching the connector member because the device body will not rotate around the wrist.

Moreover, it is preferable to provide in place of the connector member a connector cover connecting to the connector. When thus comprised and the connector member is removed during everyday living to use the wrist-worn portable device as a wristwatch, the first terminal group can be protected and the appearance is good.

For the purpose of achieving a wrist-worn portable device and a wrist-worn pulse wave measuring device suited to being worn on the wrist even when using a horizontally long main case, the present invention provides in the device body a horizontally long main case whereof the dimension in the three o'clock and nine o'clock directions of the wristwatch is longer than the dimension in the six o'clock and twelve o'clock directions, and preferably connects the wrist band to the main case at a position offset towards three o'clock from the center of the main case in the direction of three o'clock and nine o'clock.

If thus comprised, the structure of the device body will protrude greatly in the direction of nine o'clock on a wristwatch as seen from the wrist band, but there is no great protrusion in the three o'clock direction. Therefore, when the wrist-worn portable device is worn on the left hand, the wrist can be freely bent considering that a horizontally long main case is used. Moreover, because there is no great protrusion in the three o'clock direction, the back of the hand will not strike the main case even if the user falls down.

When a flat battery and flat piezoelectric element are disposed inside the main case of the device body in the present invention, the piezoelectric element and battery are preferably disposed flat inside the main case in the three and nine o'clock directions of a wristwatch. If thus comprised, a thin device body can be achieved because the battery and piezoelectric device are placed flat. Moreover, if the battery cover is disposed in the back member of the device body, a structure whereby the user can easily replace the battery can be achieved.

Furthermore, the center of gravity in the three and nine o'clock directions of a wristwatch is preferably offset from the center position in this direction toward the three o'clock position. If thus comprised, the device body can be securely attached to the arm because the wrist band is connected on the side to which the center of gravity is offset.

A wrist-worn portable device of this type can be constructed as a wrist-worn pulse wave measuring device capable of displaying such pulse information as the pulse count on the display by providing a sensor unit of which the light emitting unit and light receptor face the finger surface, a cable extending from this sensor unit for inputting the receptor results of the light receptor to the device body, and a data processing circuit contained in the device body for obtaining the pulse information to be displayed on the display based on the receptor results of the light receptor.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings, wherein like reference symbols refer to like parts,

FIGS. 1A and 1B are a descriptive diagram showing a wrist-worn pulse wave measuring device according to a preferred embodiment of the present invention when in use;

FIG. 2 is a plan view of the device body of the wrist-worn pulse wave measuring device shown in FIG. 1;

FIG. 3 is a bottom view of the device body of the wrist-worn pulse wave measuring device shown in FIG. 1;

FIG. 4 is a descriptive diagram of the device body of the wrist-worn pulse wave measuring device shown in FIG. 1 viewed from the six o'clock direction of a wristwatch;

FIG. 5 is a side view of the device body of the wrist-worn pulse wave measuring device shown in FIG. 1 taken from the three o'clock direction of a wristwatch;

FIG. 6A is a plan view of an optical unit of a sensor unit used in the wrist-worn pulse wave measuring device shown in FIG. 1; FIG. 6B is a plan view showing a sensor fastening band of the sensor unit used in the wrist-worn pulse wave measuring device when opened; and FIG. 6C is a descriptive diagram showing the structure of a separate sensor unit;

FIGS. 7A and 7B are a descriptive diagrams showing the wrist-worn pulse wave measuring device in accordance with the present invention using a different sensor fastening band;

FIG. 8 shows the wrist-worn pulse wave measuring device shown in FIG. 1 with the sensor unit attached to the finger;

FIG. 9 is a graph showing the emissions spectrum of an InGaN blue LED used in the wrist-worn pulse wave measuring device shown in FIG. 1;

FIG. 10 is a graph of the light reception characteristics of an InGaP phototransistor used in the wrist-worn pulse wave measuring device shown in FIG. 1;

FIG. 11 is a graph of the light reception characteristics of a filtered phototransistor unit used in the wrist-worn pulse wave measuring device shown in FIG. 1;

FIG. 12 is a functional block diagram of the data processing circuit of the wrist-worn pulse wave measuring device shown in FIG. 1;

FIG. 13 is an enlarged view of the connector of the wrist-worn pulse wave measuring device shown in FIG. 1 as seen from the direction of three o'clock on a wristwatch;

FIG. 14 is an electrical schematic diagram of the connector of the wrist-worn pulse wave measuring device shown in FIG. 1;

FIGS. 15A and 15B show the structure of the connector piece used in the connecting means shown in FIG. 13;

FIG. 16 depicts the structure of the connector used in the connecting means shown in FIG. 13;

FIG. 17 is a cross-sectional view illustrating the connector piece shown in FIG. 15 mounted to the connector shown in FIG. 16;

FIG. 18 is a plan view showing the positions of the electrodes in the connector piece shown in FIG. 15;

FIGS. 19A and 19B shows the structure of a connector cover covering the connector and substituted for the connector piece in the wrist-worn pulse wave measuring device shown in FIG. 1;

FIG. 20A is a graph showing the relationship between the optical wavelength and the light transmittance of the skin; FIG. 20B is a graph showing the relationship between optical wavelength and the absorption characteristics of hemoglobin;

FIG. 21 is a graph showing the light reception characteristics of a silicon phototransistor used in a conventional wrist-worn pulse wave measuring device;

FIG. 22 is a graph showing the emissions spectrum of a GaP LED used in the wrist-worn pulse wave measuring device shown in FIG. 1;

FIG. 23 is a graph of the light reception characteristics of a GaAsP phototransistor used in the wrist-worn pulse wave measuring device shown in FIG. 1; and FIG. 24 shows the turning stop construction of a conventional device body related to the referenced example.

DESCRIPTION OF THE PREFERRED EMBODIMENT

Reference is now made to FIGS. 1A and 1B, illustrating a wrist-worn pulse wave measuring device according to the preferred embodiment.

In FIG. 1A, wrist-worn pulse wave measuring device 1 (wrist-worn portable device) according to the present embodiment comprises a device body 10 having a wristwatch construction, cable 20 connected to device body 10, and sensor unit 30 provided on a digital end of this cable 20. Wrist band 12 is disposed to device body 10 wrapping around the arm from the direction of twelve o'clock on the wristwatch and fastened in the direction of six o'clock; wrist band 12 enables device body 10 to be worn freely on the arm. Referring to FIG. 1A, sensor unit 30 comprises a sensor securing band 40 approximately 10 mm wide, and sensor unit 30 is held by sensor securing band 40 on the index finger between the knuckle and first joint.

Structure of the Device Body

In FIG. 2, device body 10 comprises a watch case 11 (main case) preferably fabricated from resin with a display, preferably comprising liquid crystal display device 13 arranged on the surface side of this watch case 11 for digitally displaying the pulse count and other pulse information in addition to the current time and date. Data processing circuit 50, which is used for signal processing detection signals from, for example, sensor unit 30 to display the change in pulse count, is arranged in watch case 11. Data processing circuit 50 and liquid crystal display device 13 together comprise information display means 60. A stopwatch circuit is also included in to data processing circuit 50, enabling information display means 60 to display the normal time, lap time, split time, and other time information on liquid crystal display device 13. Button switches 111–115 for setting thetime, changing the display mode, and other functions are also provided on the outside of watch case 11. Button switches 116 and 117 are also provided on the face of watch case 11. The power supply for wrist-worn pulse wave measuring device 1 is preferable battery 59 secured inside watch case 11; cable 20 supplies power from battery 59 to sensor unit 30, and communicates detection results from sensor unit 30 to data processing circuit 50 inside watch case 11. Note that an annunciator or alarm implemented a piezoelectric device 58 is disposed to the nine o'clock side of the wristwatch relative to battery 59.

As the functions of wrist-worn pulse wave measuring device 1 are increased, it is also necessary to enlarge device body 10, but because of the limitations imposed by device body 10 being worn on the arm, device body 10 cannot be enlarged in the directions of six o'clock and twelve o'clock. A horizontally long watch case 11 in which the length dimension in the directions of three o'clock and nine o'clock is greater than the length in the directions of six o'clock and twelve o'clock is therefore used for device body 10 in the present embodiment.

Wrist band 12 is therefore connected to this watch case 11 at a position offset toward the three o'clock position from the center position C in the directions of three o'clock and nine o'clock of this watch case 11. As a result, device body 10 has a large protrusion 101 in the direction of nine o'clock on the wristwatch when seen from the wrist band 12, but does not have a similarly large protrusion in the direction of three o'clock.

As shown in FIG. 3 and FIG. 4, a flat battery 59 for the power supply and a piezoelectric device 58, preferably flat in shape, are arranged side by side in a planar direction (the directions of three o'clock and nine o'clock on the wristwatch) inside watch case 11, thereby enabling a thin profile device body 10 and, by providing battery cover 118 on back 119, a structure whereby the user can easily replace battery 59.

While battery 59 is disposed at a position offset toward three o'clock from center position C, piezoelectric device 58 is disposed at a position offset toward nine o'clock from center position C. Thus, because battery 59 is heavier than piezoelectric device 58, the center of gravity G in the directions of three o'clock and nine o'clock on device body 10 is offset from the center position C in the direction of three o'clock. As a result, wrist band 12 is connected on the side to which the center of gravity is offset.

Data processing circuit 50 comprises analog circuit circuit board 501 and digital circuit circuit board 502, and are disposed one over the other on the display surface side of piezoelectric device 58 and battery 59. Liquid crystal display device 13 is disposed thereabove on the display surface side of data processing circuit 50. As will also be shown from FIG. 4, cover glass 131 covers the outside surface side of liquid crystal display device 13.

Turning Stop Structure for the Device Body

Referring to FIG. 5, a connecting member 105 for holding the holding pin 121 attached to the end of wrist band 12 is formed on the outside of watch case 11 of device body 10 in the direction of twelve o'clock on a wristwatch. A holder 106 is formed on the outside of watch case 11 in the direction of six o'clock on the wristwatch, and a fastener 122 is attached to said holder 106; wrist band 12 is wrapped around the wrist and folded back around fastener 122 at some intermediate lengthwise position, and held by fastener 122.

Turning stop 108 is formed integrally to watch case 11 and extends at the six o'clock direction of the wristwatch of device body 10 from the edge of flat back 119 in which battery cover 118 is formed to holder 106. Turning stop 108 forms an approximately 115° angle to back 119. As a result, when wrist-worn pulse wave measuring device 1 is secured by wrist band 12 such that device body 10 is positioned at the top L1 (the same side as the back of the hand) of the left wrist L (arm), back 119 of watch case 11 is secured tightly against top L1 of wrist L, and turning stop 108 is touching side L2 on the same side of the arm as the radius R of the arm. In this position, back 119 of device body 10 straddles the radius R and ulna U of the arm through the skin, and the curved part 109 of the turning stop 108 and back 119 is against the radius R of the arm through the skin. Because turning stop 108 and back 119 form an anatomically ideal angle of approximately 115°, attempts to turn device body 10 from the position in FIG. 5 in the direction of arrow A, i.e., to turn device body 10 around wrist L from the front to the other side, are inhibited or stopped by turning stop 108 in contact with side L2 of the wrist L. In accordance with this arrangement device body 10 does not shift. Conversely, attempts to turn device body 10 in the direction of arrow B, i.e., attempts to turn device body 10 around the wrist L toward the front, are stopped by back 119 in contact with the top L1 of the wrist L, and device body 10 does not shift.

Furthermore, because device body 10 does not completely contact the entire circumference of the wrist L and there is a partial gap to the surface of the wrist L, this wearing comfort is not impaired by providing turning stop 108.

It should also be noted that, anatomically speaking, it has been confirmed that rotation of device body 10 around the wrist can be reliably prevented if the angle formed by back 119 and turning stop 108 is set in the range from approximately 105° to approximately 125°.

It should also be noted that wrist-worn pulse wave measuring device 1 may be worn with device body 10 positioned at the bottom L3 (the same side as the palm) of the wrist L, in which case turning stop 108 of device body 10 is positioned in contact with side L4 on the same side as the ulna U of the arm. Even in this position, device body 10 will not rotate unnecessarily whether force is applied in the direction of arrow A or arrow B.

Sensor Unit Configuration

FIG. 6A is a plan view of the optical unit of the sensor unit used in the wrist-worn pulse wave measuring device according to the present embodiment, FIG. 6B is a plan view showing the band for securing the sensor of this sensor unit used in this wrist-worn pulse wave measuring device when the band is laid flat, and FIG. 6C shows the structure of an alternative sensor unit.

Referring again to FIG. 1B, sensor unit 30 comprises sensor securing band 40 and optical unit 300. Sensor securing band 40 is made from a flexible, thick resin molding which is spread open from a normally circular configuration, fit over the base of the finger, and then released, allowing the inherent shape retention of the band to wrap the band around the base of the finger.

The middle part of sensor securing band 40 is even thicker, and it is there that a hole 41 for holding optical unit 300 is formed.

In FIG. 6A, optical unit 300 is enclosed in preferably, a rectangular resin molding, comprising a pair of flanges 311 and 312 arranged on the side and cable 20 leading from the inside of this optical unit 300.

In FIG. 6B, hole 41 in sensor securing band 40 is a shape and size for accommodating optical unit 300, and comprises recesses 411 and 412, in which flanges 311 and 312 are fit when optical unit 300 is fit in hole 41, to prevent optical unit 300 from falling out. Note also that constricted parts 410 are formed in four places in sensor securing band 40 to enable easier fitting to the finger.

Because it is considered sufficient to be able to lightly clench the hand when the sensor unit 30 is worn at the base of the finger, there is no problem if the width of sensor securing band 40 is approximately 20 min. A configuration in which the width of sensor securing band 40 is slightly wider in the part where optical unit 300 is held can also be used as shown in FIG. 6C. In addition, a sensor securing band 400 with a light shield support structure as shown in FIGS. 7A and 7B may also be used considering that sensor unit 30 is secured to the finger.

FIG. 8 depicts the condition in which the sensor unit is worn at the base of the finger.

Referring to FIG. 8, optical unit 300 comprises a sensor frame 301 as the case closed by bottom cover 302, thus forming a parts housing on the inside. In the top of sensor frame 301 glass plate 304 filter forms a transparent window; circuit board 305 is secured inside sensor frame 301 opposing this glass plate 304. LED 31, phototransistor 32, transisters (not shown), and other electronic components are mounted on circuit board 305 with LED 31 and phototransistor 32 oriented with the light emitting face and receptor face, respectively, facing glass plate 304.

In this embodiment an InGaN (indium-gallium-nitrogen) blue LED is used for LED 31; the emissions spectrum of this LED has an emissions peak at 450 nm as shown in FIG. 9, and a wavelength range from 350 nm to 600 nm. Corresponding to LED 31 with these emissions characteristics, a GaAsP (gallium-arsenic-phosphorus) phototransistor is used as phototransistor 32; the detection range of this element has a primary sensitivity range from 300 nm to 600 nm with a sensitivity also extending below 300 nm. It is also possible to use as phototransistor 32 a sensor unit adding a filter to this element; the detection range of such a sensor unit has, as shown in FIG. 11, a primary sensitivity range from 400 nm to 550 nm. Because the power consumption of LED 31 and phototransistor 32 is relatively low, the continuous operating time is long even when both the clock function and pulse wave measuring device function are driven with a single compact battery as in wrist-worn pulse wave measuring device 1 according to the present embodiment.

Because optical unit 300 is arranged on sensor securing band 40 such that glass plate 304 faces the inside, if sensor securing band 40 is worn at the base of the finger, the light emitting surface and receptor surface of LED 31 and phototransistor 32, respectively, also face the surface of the skin. Therefore, when light is emitted from LED 31 toward the finger, the light reflected from the body (blood vessels) is detected by phototransistor 32, optical unit 300 inputs the detection result (pulse signal) to device body 10 via cable 20, And the pulse count can be obtained from the pulse signal by device body 10.

Data Processing Circuit Configuration

Referring to FIG. 12, a functional block diagram of the data processing circuit in the watch case, the pulse signal converter 51 of data processing circuit 50 converts the signal input from sensor unit 30 by cable 20 to a digital signal, and outputs to pulse signal memory 52. Pulse signal memory 52 is memory, such as RAM, storing the pulse data converted to digital signals. Pulse signal calculator 53 reads and, analyzes the frequency of the signal stored in pulse signal memory 52, and inputs the result to pulse component extractor 54. Pulse component extractor 54 extracts the pulse component from the input signal from pulse signal calculator 53, and outputs to pulse rate calculator 55. This pulse rate calculator 55 calculates the pulse count based on the input pulse wave frequency component, and outputs the result to liquid crystal display device 13.

Connector Configuration

FIG. 13 is an enlarged view from three o'clock on the wristwatch with the connector piece fit to the connector member. FIG. 14 illustrates the combination of sensor circuit electrodes on the connector piece side, and the connector member terminals for communicating signals with the sensor circuit.

So that wrist-worn pulse wave measuring device 1 according to the present embodiment can normally be used as a common wristwatch, cable 20 and sensor unit 30 can be connected and disconnected at the side of device body 10, positioned near six o'clock on the wristwatch. More specifically, a connector 70 is formed on the outside surface of the part extended as turning stop 108 at the six o'clock position of a wristwatch on the edge of device body 10 such that connector piece 80 (connector member) disposed on the end of cable 20 can be fit thereto as shown in FIG. 13.

The electrical connections completed between connector 70 and connector piece 80 in a connector means using connector 70 and connector piece 80 are as shown in FIG. 14.

Referring to FIG. 14, terminals 751–756 (first terminal group) are disposed on connector 70, which is provided on the device body 10 side, and electrodes 831–836 (second terminal group) corresponding to these terminals 751–756 are disposed to connector piece 80. As a result, when connector piece 80 is connected to connector 70, electrodes 831–836 are respectively electrically connected to terminals 751–756. Of these, terminal 751 is a positive terminal for supplying second drive voltage $V_{DD}$ to LED 31 through electrode 832; terminal 753 is a terminal set to the negative potential of LED 31 through electrode 833; terminal 754 is a terminal for supplying the constant drive voltage $V_{REG}$ to the collector terminal of phototransistor 32 through electrode 834; terminal 751 is the terminal to which the signal from the emitter terminal of phototransistor 32 is input through electrode 831; and terminal 755 is the terminal to which is input through electrode 835 the signal for detecting whether connector piece 80 is connected to connector 70. Electrode 836 grounds sensor unit 30 to the body, and shields electrodes 831–836 by making $V_{DD}$ the ground when terminal 756 and electrode 836 are electrically connected.

A first capacitor C1 and first switch SW1 are inserted between the LED 31 terminals (between electrodes 832 and 833) in connector piece 80. Switch SW1 is closed when connector piece 80 is disconnected from connector 70, connecting first capacitor C1 parallel to LED 31, and is open when connector piece 80 is connected to connector 70. A second capacitor C2 and second switch SW2 are similarily inserted between the terminals (electrodes 831 and 834) of phototransistor 32. This switch SW2 is closed when connector piece 80 is disconnected from connector 70, connecting the second capacitor C2 parallel to phototransistor 32, and is open when connector piece 80 is connected to connector 70.

The structure of the connector means whereby connector piece 80 is connected to and disconnected from connector 70 thus comprised is described further below with reference to FIGS. 15A, 15B–FIG. 18.

FIGS. 15A and 15B are enlarged views looking from the top and bottom, respectively, showing the construction of the connector piece disposed at the end of the cable, FIG. 16 is an enlarged view of the connector on the device body, FIG. 17 is a vertical cross-sectional view showing the connector piece connected to the connector, and FIG. 18 illustrates the circuit pattern and placement of the electrodes in the connector piece.

Referring to FIGS. 15A and 15B, a pair of projections 81 and 82 projecting downward is formed on both sides of the bottom 801 of connector piece 80. Four engaging members 811, 812, 821, and 822 (second group of engaging claws) project toward the inside at the bottoms of these projections 81 and 82.

Six electrodes 831, 832, 833, 834, 835, 836 (second terminal group) are formed on the bottom 801 of connector piece 80, and an annular ridge member 841, 842, 843, 844, 845, and 846 is formed around each electrode. Thus, as described below, when connector piece 80 is mounted on connector 70, connector piece 80 is slid in the direction of arrow Q after engaging connector piece 80 with connector 70, but electrodes 831–836 are formed in two rows of electrodes 831, 833, and 833, and electrodes 834, 835, and 836 in this sliding direction (the direction of arrow Q). In addition, the electrodes 831–836 in each row are arranged at an angle offset in a direction intersecting the sliding direction (direction of arrow Q) of connector piece 80.

Two operating pins 837 and 838 for switching a circuit blocking the effects of static electricity when cable 20 is connected to device body 10 are also provided on the bottom of connector piece 80. As described below with reference to FIG. 17, these operating pins 837 and 838 project from bottom 801 of the connector piece when connector piece 80 is removed from connector 70.

As shown in FIG. 16, engaging parts 71, 72, 73, and 74 (first group of engaging claws) projecting to the outside are formed on the sides of connector 70 of device body 10. Therefore, if, after fitting connector piece 80 down over connector 70 such that projections 81 and 82 of connector piece 80 are positioned outside engaging parts 71, 72, 73, and 74 of connector 70, and engaging members 811 and 821 of connector piece 80 are positioned between engaging parts 71 and 72 and engaging parts 73 and 74, respectively, connector piece 80 is pushed towards connector 70 such that engaging members 811 and 821 pass between engaging parts 71 and 72 and engaging parts 73 and 74, respectively, (the first operation for connecting connector piece 80 to connector 70), and connector piece 80 is then slid in the direction of arrow Q (the mounting direction for connector piece 80, the direction from six o'clock to twelve o'clock of device body 10), engaging members 811, 821 become seated below engaging parts 71 and 73. Engaging members 812 and 822 are also seated below engaging parts 72 and 74. As a result, engaging members 811, 821, 812, and 822 hold engaging parts 71, 72, 73, and 74 between engaging members 811, 821, 812, and 822 and bottom 801 of connector piece 80, and connector piece 80 can be easily and reliably connected to connector 70.

It should also be noted that terminals 751–756, like electrodes 831–836, are formed in two rows of terminals 751, 752, and 753 and terminals 754, 755, and 756 in the sliding direction of connector piece 80 (the direction of arrow W). Each of these rows of terminals 751–756 is, like electrodes 831–836, arranged at an angle offset in a direction intersecting the sliding direction (direction of arrow Q) of connector piece 80. Therefore, when connector piece 80 is mounted on connector 70, the six terminals 751–756 are electrically connected to the six electrodes 831–836, respectively, and the measurement result from sensor unit 30 can be input to device body 10 through cable 20.

It should be noted that because terminals 751–756 and electrodes 831–836 are arranged in two rows in the sliding direction of connector piece 80, and the positions between each of the terminals and each of the electrodes are diagonally offset in a direction intersecting this sliding direction, non-corresponding terminals 751–756 and electrodes 831–836 will not contact even when connector piece 80 is slid across connector 70. Moreover, because the terminals and electrodes can be separated from each other even when the area of connector 70 is confined, shorting between terminals and between electrodes does not easily occur even if water penetrates between connector piece 80 and connector 70. Furthermore, because terminals 752, 754, and 756, and electrodes 832, 834, and 836 to which the drive voltage is applied can, in particular, be arranged at separated positions, even if water does penetrate between connector piece 80 and connector 70, tracking in particular will not occur between different-potential terminals and electrodes. As a result, an overvoltage will not be applied to LED 31 or phototransistor 32.

When connector piece 80 is disconnected from connector 70, connector piece 80 is slid in the opposite direction in the direction of arrow R. As a result, engaging members 811, 821 return to the positions between engaging parts 71 and 72 and engaging parts 73 and 74. As a result, connector piece 80 can be easily and reliably removed from connector 70 by simply lifting connector piece 80 up.

Engaging mechanism 700 is thus comprised such that connector piece 80 is engaged with and held on connector 70 when connector piece 80 is slid across connector 70, and this engaged state is released when connector piece 80 is slid from this state in the opposite direction (the direction of arrow R). The engaging mechanism thus comprised reliably engages even while using few parts.

Stopper Mechanism Configuration

As will be known from FIG. 16, continuous vertical faces 711, 721, 731, and 741 are formed on the sides of engaging parts 71–74 in the direction of arrow Q when viewed from the side. Therefore, if when mounting connector piece 80 on connector 70 connector piece 80 is slid in the direction of arrow R (second operation), engaging members 811, 812, 821, and 822 respectively contact vertical faces 711, 721, 731, and 741, thus stopping connector piece 80 in the mounted position on connector 70. Vertical faces 711, 721, 731, and 741 therefore function as a first stopper for connector piece 80.

Conversely, when connector piece 80 is slid in the direction of arrow R for removal from connector 70, engaging members 811, 821 contact the backs of vertical faces 721 and 741 of engaging parts 72 and 74, thus stopping connector piece 80 in the original position on connector 70. Therefore, the backs of vertical faces 721 and 741 function as second stoppers for connector piece 80.

In addition, the user can easily connect and disconnect connector piece 80 on connector 70. The connector 70 and other parts will also not be damaged because the user cannot accidentally apply too much force.

Construction of Terminals and Electrodes

In connector 70, terminals 751–756 are each disposed inside holes 761, 762, 763, 764, 765, and 766 formed in connector 70. A cross-sectional view through where terminals 753 and 756, operating pin 838, and electrodes 833 and 836 are formed is shown in FIG. 17.

As shown in FIG. 17, connector piece 80 is constructed with cover member 806 15 covering outside case 805 in which circuit board 85 can be housed. Holes 863 and 866 are formed in cover member 806, and annular ridge members 843 and 846 are formed around the open lip on the downside of the holes. Electrodes 833 and 836 are disposed inside holes 863 and 866. Electrode 833 is secured by for example screw 881, and electrode 836 is secured between circuit board 85 and cover member 806. A water-resistant packing 873 and 876 is also fit to electrodes 833 and 836. Electrodes 833 and 836 are electrically connected to the circuit pattern of circuit board 85 disposed inside connector piece 80. This electrical structure is the same for the electrodes other than electrodes 833 and 836, i.e., electrodes 831, 832, 834, and 835. Note that the wire of cable 20 is also electrically connected to the circuit pattern on circuit board 85 by soldering.

Click Mechanism Configuration

Connector 70 is constructed with the recess therein covered by cover member 706. Holes 763 and 766 are formed in cover member 706. Inside these holes 763 and 766 terminals 753 and 756 are disposed as retractable pins of which the tips project from holes 763 and 766. A coil spring 773 and 776 is disposed to the flange 783 and 786 formed at the base end of each terminal 753 and 756, and terminals 753 and 756 are pushed in the direction protruding from holes 763 and 766 by coil springs 773 and 776. However, because the outside diameter of flanges 783 and 786 is greater than the inside diameter of holes 763 and 766, terminals 753 and 756 will not slip out from holes 763 and 766. This terminal structure is the same for the terminals other than terminals 753 and 756, i.e., terminals 751, 752, 754, and 755.

With a terminal structure thus comprised, because connector piece 80 is slid over connector 70 when connector piece 80 is mounted to connector 70, terminals 753 and 756 move over annular ridge members 843 and 846 of connector piece 80 while being pushed out by coil springs 773 and 776, and positively contact electrodes 833 and 836. Because a click configuration is achieved by using annular ridge members 843 and 846, terminals 753 and 756, and coil springs 773 and 776 as is, connector piece 80 can be reliably connected to connector 70. Note that to achieve a click configuration of this type it is also possible to provide terminals using retractable pins on the connector piece 80 side, and provide the annular ridge members on the connector 70, opposite the arrangement of the present embodiment.

Switch Mechanism Configuration

Hole 868 is also formed in cover member 806 of connector piece 80, and operating pin 838 is disposed in this hole 838. This operating pin 838 is disposed to be retractable inside hole 868 in a manner with the tip thereof projecting from hole 868. A leaf spring type switch spring 88 is disposed to flange 898 formed on the base of operating pin 838. Spring 88 pushes operating pin 838 by means of the end 885 thereof in the direction projecting from hole 868. However, because the outside diameter of flange 898 is greater than the inside diameter of hole 868, operating pin 838 will not slip out from hole 868. Switch spring 88 is fastened with the base thereof held by screw 881 to the top of operating pin 838, and is thus electrically connected to electrode 833.

In FIG. 18, end 885 of switch spring 88 comprises contact part 886 for contacting the base of operating pin 838, and contact 887 formed on the part extending to the side therefrom. This contact 887 is electrically connected to circuit pattern 852 of circuit board 85. While not shown in the figure, this circuit pattern 852 is inserted between first capacitor C1 and electrode 833.

Therefore, when connector piece 80 is not mounted on connector 70, operating pin 838 is pushed by switch spring 88 and the end projects from hole 868 as shown in FIG. 17, and in this state contact 887 of switch spring 88 is electrically connected to circuit pattern 852 of circuit board 85. More specifically, first switch SW1 closes in conjunction with the movement of operating pin 838 shown by the arrow in FIG. 14, and first capacitor C1 becomes electrically connected in parallel to LED 31. As a result, even if a high potential charge caused by static electricity contacts electrodes 832 and 833, the charge is stored to first capacitor C1, and LED 31 is not damaged.

When connector piece 80 is mounted on connector 70, operating pin 838 moves in the direction drawing into hole 868 as shown by the dot-dot-dash line in FIG. 17, and switch spring 88 is deformed as shown by the dot-dot-dash line. When switch spring 88 is thus deformed, contact 887 lifts from circuit pattern 852 of circuit board 85, and the electrical connection is broken. Specifically, when connector piece 80 is mounted to connector 70, first switch SW1 in FIG. 14 is open, and a circuit configuration capable of measuring the pulse is completed. In addition, even if a charge is stored to first capacitor C1, the charge will not be discharged through electrodes 832 and 833 and terminals 752 and 753, and the circuits contained in connector 70 and device body 10 will not be damaged.

Furthermore, while this switch configuration is simple, it reliably tracks the mounting operation of connector piece 80 to connector 70.

It should also be noted that a switching mechanism of this configuration is also formed for phototransistor 32 as shown in FIG. 14. As will be known from FIG. 18, the configuration of this switching mechanism comprises an operating pin 837 and switch spring 89 similarly to the switching mechanism for LED 31, and further description thereof is therefore omitted below.

Connector Cover Configuration

FIGS. 19A and 19B illustrate the configuration of connector cover 90, which is mounted to connector 70 in place of connector piece 80 when cable 20 and sensor unit 30 are removed from wrist-worn pulse wave measuring device 1, and wrist-worn pulse wave measuring device 1 is used as a regular wristwatch. Because, unlike connector piece 80, connector cover 90 does not require electrodes, a sensor circuit, and a cable, connector cover 90 is thinner overall and is shaped to not detract from the appearance when mounted to connector 70. However, the structure whereby connector cover 90 is mounted to connector 70 is the same as that of connector piece 80. Specifically, a pair of projections 91 and 92 projecting downward is formed on both sides of the bottom 901 of connector cover 90. Four engaging members 911, 912, 921, and 922 (second group of engaging claws) project toward the inside at the bottoms of these projections 91 and 92. Annular ridge members 941–946 forming a click mechanism with terminals 751–756 are formed on bottom 901 at the positions to which terminals 751–756 of connector 70 are disposed.

As with connector piece 80, when connector piece 90 is mounted on connector 70, after fitting connector cover 90 down over connector 70 such that engaging members 911 and 921 of connector cover 90 are positioned between engaging parts 71 and 72 and engaging parts 73 and 74, respectively, connector cover 90 is pushed towards connector 70 such that engaging members 911 and 921 pass between engaging parts 71 and 72 and engaging parts 73 and 74, respectively, connector cover 90 is then slid in the direction of arrow Q (the direction from six o'clock to twelve o'clock of device body 10), and engaging members 911, 921 become seated below engaging parts 71 and 73. Engaging members 912 and 922 are also seated below engaging parts 72 and 74. As a result, engaging members 911, 921, 912, and 922 hold engaging parts 71, 72, 73, and 74 between [engaging members 911, 921 912, and 922 and] bottom 901 of connector cover 90, and terminals 751–756 of connector 70 ride over annular ridge members 941–946, exhibiting a click force. Connector cover 90 is thus mounted on connector 70.

Operation

The operation of wrist-worn pulse wave measuring device 1 thus comprised is described briefly below with reference to FIGS. 1A and 1B and FIG. 8.

Referring first to FIG. 1, when wrist-worn pulse wave measuring device 1 is used as a conventional wristwatch, device body 10 is held on the arm by means of wrist band 12 with cable 20 and sensor unit 30 removed from connector 70 of device body 10. At this time connector cover 90 shown in FIG. 19 is mounted on connector 70, thus improving the appearance and protecting connector 70.

When the pulse rate is measured while running using wrist-worn pulse wave measuring device 1, connector piece 80 is mounted on connector 70 to connect cable 20 to device body 10, and device body 10 is then secured to the arm using wrist band 12. Sensor unit 30 (glass plate 304 of optical unit 300) is then secured tightly to the finger by sensor securing band 40, and the user goes running.

When light is emitted toward the finger from LED 31 in this state as shown in FIG. 8, the light reaches the blood vessels, part of the light is absorbed by hemoglobin in the blood, and part is reflected. The light reflected from the finger (blood vessels) is detected by phototransistor 32, and the change in detected light quantity corresponds to the blood volume changes resulting from the blood pulse. Specifically, when the blood volume is great, the reflected light is weak; when the blood volume decreases, the reflected light becomes stronger. As a result, the pulse rate, etc., can be detected by monitoring the change in reflected light intensity with phototransistor 32. To accomplish such detection, the signal input from phototransistor 32 (sensor unit 30) is converted to a digital signal, and the pulse count is calculated by data processing circuit 50 shown in FIG. 12 performing frequency analysis or other analyses on this digital signal. The pulse count obtained from this calculation is then displayed on liquid crystal display device 13. In short, wrist-worn pulse wave measuring device 1 functions as a pulse wave measuring device.

Referring again to FIG. 8, part of the light emitted from LED 31 travels through the finger and reaches the blood vessels as shown by arrow C, and the reflected light from the hemoglobin in the blood travels back to phototransistor 32 as shown by arrow D. The light quantity detected by this path is the "bioreflection." Part of the light emitted from LED 31 is also reflected at the finger surface as shown by arrow E, and travels back to phototransistor 32. The light quantity detected by this path is the skin reflection. Part of the light emitted from LED 31, and part of the light reflected from the blood vessels, is absorbed or diffused inside the finger as shown by arrows F and G, and does not reach phototransistor 32.

Sensor unit 30 uses LED 31 with an emissions wavelength range from 350 nm to 600 nm, and phototransistor 32 with a detection wavelength range from 300 nm to 600 nm, and the biological data is expressed based on the detection results in the overlapping wavelength range from approximately 300 nm to approximately 600 nm. Using such a sensor unit 30, light in the wavelength range below approximately 700 nm contained in the external light does not reach phototransistor 32 (photodetector) using the finger as an optical conductor, and virtually all light below 300 nm is absorbed by the skin surface. As a result, the detection results are not affected by external light, and the biological data can be measured from the detection results in the wavelength range from approximately 300 nm to approximately 600 nm based only on the light from the emitter. It should be noted that, because the pulse information is obtained without being affected by external light, it is possible to use for LED 31 a device having an emissions wavelength range from 300 nm to 700 nm and as phototransistor 32 a device with a detection wavelength range below 700 nm.

Effects of the Embodiment

In wrist-worn pulse wave measuring device 1 (a wrist-worn portable device) according to the present embodiment as described above, turning stop 12 will not move up from side L2 of wrist L, and back 119 will not move any farther from top L1 of wrist L even if device body 10 is pushed in the direction of arrow A or arrow B as described with reference to FIG. 5 because device body 10 comprises turning stop 108 at an anatomically ideal angle of approximately 115° to back 119. Therefore, because device body 10 will not shift even if the user goes running with wrist-worn pulse wave measuring device 1 worn on the arm, the liquid crystal display device 13 can always be viewed by simply bending the elbow slightly. Moreover, it does not feel is comfortable from sweat because device body 10 is not tight to the skin all the way around the wrist and there is a partial gap to the surface of the wrist L. Furthermore, rotation is only controlled at two places on one side around the wrist by back 119 and turning stop 108. As a result, even when the arm is thin back 119 and turning stop 108 positively contact the arm and the turning stop effect is reliably achieved, and when the arm is thick there is no constricted feeling. Moreover, turning stop 108 may be integrally formed as an extension of watch case 11. As a result, unnecessary rotation of device body 10 can be reliably prevented at low cost and without impairing comfort by simply improving the shape of device body 10 in a wrist-worn pulse wave measuring device 1 according to the present embodiment.

Furthermore, because a connector means (connector 70 and connector piece 80) is provided for cable 20 leading from sensor unit 30 enabling this cable 20 to be connected to device body 10 and disconnected from device body 10, if sensor unit 30 and cable 20 are removed from device body 10, it can be conveniently used as a regular wristwatch.

Moreover, because connector 70 is formed in the surface member at the part corresponding to turning stop 108, the part extended to provide turning stop 108 can be directly used as connector 70. It is therefore not necessary to provide extraneous projections to device body 10. Moreover, because connector 70 is positioned in the direction of six o'clock on a wristwatch, connector 70 is to the front as seen by the user when device body 10 is worn on the arm, and operation is simple. Furthermore, because connector 70 does not project from device body 10 in the direction of three o'clock on the wristwatch, the user can freely move the wrist while running, and the back of the hand will not contact connector 70 even if the runner falls while running. It is, therefore, safe for the user and connector 70 is not damaged. Moreover, because connector 70 and connector piece 80 are connected by an engaging mechanism, cable 20 will not be accidentally disconnected while running.

Furthermore, while connector piece 80 is mounted on connector 70 by sliding it over connector 70 from the direction of six o'clock in the direction of twelve o'clock on a wristwatch, the force applied to device body 10 at this time is in a direction whereby device body 10 rotates more difficulty as a result of turning stop 108. Therefore, because device body 10 does not turn around the wrist when connector piece 80 is mounted, mounting is simple.

Moreover, in a wrist-worn pulse wave measuring device 1 according to the present embodiment, a horizontally long watch case 11 is provided for device body 10, and wrist band 12 is connected to this watch case 11 at an offset position in the direction of three o'clock. As a result, when wrist-worn pulse wave measuring device 1 is held on the left wrist by wrist band 12, there is no large projection in the direction of three o'clock as shown in FIG. 2 and FIG. 3. Comfort is therefore good because, for example, the wrist can be freely bent despite using a horizontally long watch case 11. Furthermore, the back of the hand will not strike watch case 11 if the user falls down because there is no large projection in the direction of three o'clock. In addition, because large protrusion 101 positioned in the direction of nine o'clock is supported tight to the surface of the arm on the elbow side, wrist-worn pulse wave measuring device 1 is stable. It is therefore not necessary to use an unnecessarily wide wrist band 12 even if a horizontally long watch case 11 is used.

Device body 10 can be made thin because battery 59 and piezoelectric device 58 are positioned inside watch case 11 side by side in the directions of three o'clock and nine o'clock using the fact that watch case 11 is horizontally long. Furthermore, because battery 59 and piezoelectric device 58 are offset from each other, the user can easily replace battery 118 by removing battery cover 118.

Moreover, the center of gravity G in the directions of three o'clock and nine o'clock is offset towards three o'clock, and wrist band 12 is connected on the side to which this center of gravity is offset. As a result, device body 10 can be worn stably on the arm.

In addition, the emissions wavelength range of LED 31 in wrist-worn pulse wave measuring device 1 according to this embodiment is in the range from 350 nm to 600 nm, and the detection wavelength range of phototransistor 32 has the primary sensitivity range from 300 nm to 600 nm. On the other hand, the detection wavelength range when a unit combining an element and filter is used as phototransistor 32 is in the range from 400 nm to 550 nm. Therefore, even if the pulse wave is measured using a simple light shield as shown in FIG. 1A, 1B, and FIG. 7, light with a wavelength below 700 nm contained in the external light does not impinge phototransistor 32 (photodetector) passing through the finger as an optical conductor and only light in the wavelength range not affecting the detection result passes through the finger as an optical conductor. As a result, because the effects of external light do not bear on the pulse wave detection results even when external light contacts the exposed part of the finger, a sensor unit 30 blocking the detector by means of a narrow sensor securing band 40 can be used. Thus, if the sensor unit 30 is small as in the present embodiment, there is no interference with running because the hand can be closed with [sensor unit 30] worn at the base of the finger. Furthermore, because cable 20 can be shortened if sensor unit 30 is worn at the base of the finger, cable 20 will not get in the way while running. Wrist-worn pulse wave measuring device 1 according to the present embodiment is therefore suitable for measuring such things as the pulse count while running.

Furthermore, if the temperature distribution from the palm to the fingertip is measured, the temperature of the fingertip drops rapidly when it is cold while there is a relatively small drop in the temperature at the base of the finger. In other words, when it is cold, there is not a sharp drop in circulation at the base of the finger. Therefore, if sensor unit 30 is worn at the base of the finger, the pulse rate can be reliably measured even when running outdoors on a cold day.

Moreover, the signal-to-noise (S/N) ratio of the pulse signal based on the blood volume change is high because the pulse wave information is obtained using light in the wavelength range from approximately 300 nm to approximately 700 nm.

The reasons for this are described below.

The reason why wrist-worn pulse wave measuring device 1 is not easily affected by external light is described first with reference to FIG. 20A. The relationship between optical wavelength and the optical transmittance of the skin is shown in FIG. 20A. In this figure, dotted line a indicates the transmittance characteristic with 200 nm wavelength light; dotted line b, the transmittance characteristic with 300 nm wavelength light; dotted line c, the transmittance characteristic with 500 nm wavelength light; dotted line d, the transmittance characteristic with 700 nm wavelength light; and dotted line e, the transmittance characteristic with 1 μm wavelength light. As will be obvious from this figure, because light in the wavelength range below 700 nm contained in external lighting tends not to pass easily through the finger, external light incident to a part of the finger not covered by sensor securing band 40 will not pass through the finger to phototransistor 32 as shown by dotted line X in FIG. 8. Thus, because the effects of external light can be suppressed by only coveting the smallest necessary area of the finger rather than covering a large area, if light below 700 nm is used as the detection light as in this embodiment, wrist-worn pulse wave measuring device 1 according to the present embodiment can be used outdoors. It should be noted that because virtually all light in the low wavelength range below 300 nm is absorbed at the surface of the skin, the actual detection wavelength range is 300 nm–700 nm even if the detection wavelength range is simply below 700 nm.

On the other hand, if an LED with an emissions peak near 880 nm and a silicon phototransistor are used, the detection wavelength range will range from 350 nm to 1200 nm as shown in FIG. 21. Detection errors caused by variations in the external light can therefore occur easily because with a conventional optical system (detection device), external light with a wavelength of 1 μm will easily pass through the finger as an optical conductor and reach the photodetector as shown by arrow Y in FIG. 8, i.e., the pulse wave is detected based on the detection results obtained by the light indicated by dotted line e in FIG. 20A.

The reason for a high signal-to-noise (S/N) ratio in the pulse signal with wrist-worn pulse wave measuring device 1 according to the present embodiment is described next with reference to FIG. 20B. FIG. 20B is a graph showing the relationship between optical wavelength and the absorption characteristics of various hemoglobins.

In FIG. 20B, the absorption characteristic of hemoglobin not bonded with oxygen is shown by curve Hb, and the absorption characteristic of hemoglobin bonded with oxygen is shown by curve HbO2. As these curves show, the absorption coefficient of hemoglobin in the blood to light of a wavelength from 300 nm to 700 nm is great, and is several times to approximately 100 times the absorption coefficient with conventionally detected light, 880 nm wavelength light. The detection rate (S/N ratio) of the pulse based on the blood volume change is therefore high because the detection value varies sensitively to the blood volume change if light in the wavelength range for which the absorption coefficient is high (300 nm–700 nm) is used as the detected light based on the absorption characteristics of hemoglobin.

It should also be noted that a GaP LED having a primary emissions range from 540 nm to 570 nm as shown in FIG. 22, and a GaP phototransistor having a sensitivity range from 200 nm to nearly 700 nm as shown in FIG. 23, may also be used as the optical unit.

While the invention has been described in conjunction with a specific embodiment it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. wrist-worn portable device, comprising:
   a device body comprising:
      a main case including a turning stop extending therefrom in a substantially 6 o'clock direction thereof for controlling rotation of said device body when worn around a wrist of a user;
      a back member, connected to said main case, having a shape to accommodate a top of the wrist of the user; and
      a display unit arranged in said main case for displaying information;
      wherein a center of gravity of said device body in a three and nine o'clock directions on said wrist-worn portable device is offset from a center position in the three o'clock direction; and
   a wrist band operatively coupled to said main case for detachably securing said device body to the user.

2. A wrist-worn portable device according to claim 1, wherein said turning stop extends at an angle within the range from approximately 105° to approximately 125° to a back member of said main case.

3. A wrist-worn portable device according to claim 1, wherein said main case further comprises a data processing circuit;
   wherein said wrist-worn portable device further comprises
      a sensor unit having a light emitting unit and a light receptor facing a finger surface of the user;
      a cable extending from said sensor unit for electrically connecting said light receptor to said data processing circuit; and
      wherein said display unit displays pulse information in accordance with said data processing circuit and said light receptor.

4. A wrist-worn portable device according to claim 3, further comprising connecting means enabling said cable to be freely connected to said device body.

5. A wrist-worn portable device, comprising:
   a device body comprising:
      a main case comprising a turning stop extending therefrom in a substantially 6 o'clock direction thereof for controlling rotation of said device body when worn around a wrist of a user;
      a data processing circuit; and
      a back member, connected to said main case, having a shape to accommodate a top of the wrist of the user; and
      a display unit arranged in said main case for displaying information;
      wherein a center of gravity of said device body in a three and nine o'clock directions on said wrist-worn portable device is offset from a center position in the three o'clock direction;
   a wrist band operatively coupled to said main case for detachably securing said device body to the user;
   a sensor unit having a light emitting unit and a light receptor facing a finger surface of the user;
   a cable extending from said sensor unit for electrically connecting said light receptor to said data processing circuit; wherein said display unit displays pulse information in accordance with said data processing circuit and said light receptor; and
   connecting means enabling said cable to be freely connected to said device body, comprising:
      a connector comprising a first terminal group disposed on a surface of said device body at a portion thereof corresponding to said turning stop;
      a connector member formed at an end of said cable and comprising a second terminal group for electrically connecting with said first terminal group when connected to said connector; and
      an engaging mechanism for detachably securing said connector member to said connector by partially engaging said connector member and connector.

6. A wrist-worn portable device according to claim 5, wherein said engaging mechanism partially engages said connector member and connector when said connector member is slid over said connector in the six o'clock direction to twelve o'clock direction on said wrist-worn portable device.

7. A wrist-worn portable device according to claim 5, further comprising a connector cover to be engaged with said connector when said connector is disengaged from said connector member.

8. A wrist-worn portable device according to claim 1, wherein
   said device body comprises a horizontally long main case, wherein a dimension in three o'clock and nine o'clock directions is longer than a dimension in the six o'clock and twelve o'clock directions, and
   said wrist band is connected to said main case at a position offset in the three o'clock direction from the center position of said main case in the three o'clock and nine o'clock directions.

9. A wrist-worn portable device according to claim 8, wherein said main case comprises a flat battery and a flat piezoelectric element, said piezoelectric element and battery being arranged inside said main case in the three and nine o'clock directions on said wrist-worn portable device.

10. A wrist-worn portable device, comprising;
a device body comprising:
- a main case having a back member having a shape to accommodate a top of a wrist of a user;
- a display unit arranged in said main case for displaying information; and
- a turning stop extending from said main case in a substantially 6 o'clock direction of said wrist-worn portable device for controlling rotation of said device body around the wrist by contacting one side of the wrist; and a wrist band operatively coupled to said main case for detachably securing said device body to the user;

wherein said device body comprises a horizontally long main case, wherein a dimension in three o'clock and nine o'clock directions is longer than a dimension in the six o'clock and twelve o'clock directions;

wherein said wrist band is connected to said main case at a position offset in the three o'clock direction from the center position of said main case in the three o'clock and nine o'clock directions; and wherein a center of gravity of said device body in the three and nine o'clock directions on said wrist-worn portable device is offset from a center position in the three o'clock direction.

11. A wrist-worn portable device according to claim 8, wherein said main case comprises a data processing circuit;

wherein said wrist-worn portable device further comprises
- a sensor unit having a light emitting unit and a light receptor facing a finger surface of the user;
- a cable extending from said sensor unit for electrically connecting said light receptor to said data processing circuit; and wherein said display unit displays pulse information in accordance with said data processing circuit and said light receptor.

* * * * *

UNITED STATES PATENT AND TRADEMARK OFFICE
CERTIFICATE OF CORRECTION

PATENT NO.     : 5,735,800
DATED          : April 07, 1998
INVENTOR(S)    : Naoaki Yasukawa, et al.

It is certified that errors appear in the above identified patent and that said Letters Patent is hereby corrected as shown below:

Column 19, line 33, insert --A-- before "wrist-worn".

Signed and Sealed this

Twenty-seventh Day of October, 1998

Attest:

BRUCE LEHMAN

*Attesting Officer*   *Commissioner of Patents and Trademarks*